US008214030B2

(12) United States Patent
Hause, Jr. et al.

(10) Patent No.: US 8,214,030 B2
(45) Date of Patent: Jul. 3, 2012

(54) IONTOPHORESIS APPARATUS AND METHOD

(75) Inventors: Robert F. Hause, Jr., Bountiful, UT (US); Jon E. Beck, Salt Lake City, UT (US)

(73) Assignee: Encore Medical Asset Corporation, Henderson, NV (US)

( * ) Notice: Subject to any disclaimer, the term of this patent is extended or adjusted under 35 U.S.C. 154(b) by 408 days.

(21) Appl. No.: 11/733,700

(22) Filed: Apr. 10, 2007

(65) Prior Publication Data
US 2008/0058700 A1   Mar. 6, 2008

Related U.S. Application Data

(60) Provisional application No. 60/842,421, filed on Sep. 6, 2006.

(51) Int. Cl.
*A61N 1/30* (2006.01)
(52) U.S. Cl. ......................................................... 604/20
(58) Field of Classification Search ...................... 604/20
See application file for complete search history.

(56) References Cited

U.S. PATENT DOCUMENTS

| | | | |
|---|---|---|---|
| 4,141,359 A | 2/1979 | Jacobsen et al. | |
| 4,767,402 A | 8/1988 | Kost et al. | |
| 5,013,293 A | 5/1991 | Sibalis | |
| 5,019,034 A | 5/1991 | Weaver et al. | |
| 5,125,894 A | 6/1992 | Phipps et al. | |
| 5,167,617 A * | 12/1992 | Sibalis | 604/20 |
| 5,169,384 A | 12/1992 | Bosniak et al. | |
| 5,246,418 A | 9/1993 | Haynes et al. | |
| 5,254,081 A | 10/1993 | Maurer et al. | |
| 5,431,625 A | 7/1995 | Fabian et al. | |
| 5,562,607 A | 10/1996 | Gyory | |
| 5,622,530 A | 4/1997 | Phipps | |
| 5,700,481 A * | 12/1997 | Iga et al. | 424/449 |
| 5,795,293 A | 8/1998 | Carim et al. | |
| 5,895,369 A * | 4/1999 | Flower | 604/20 |
| 5,947,921 A | 9/1999 | Johnson et al. | |
| 5,978,701 A | 11/1999 | Johnson et al. | |
| 5,980,934 A * | 11/1999 | Reber et al. | 424/449 |
| 5,983,130 A | 11/1999 | Phipps et al. | |
| 5,983,133 A | 11/1999 | Garde et al. | |
| 6,009,344 A * | 12/1999 | Flower et al. | 604/20 |
| 6,047,208 A | 4/2000 | Flower | |
| 6,167,301 A | 12/2000 | Flower et al. | |
| 6,190,315 B1 | 2/2001 | Kost et al. | |
| 6,882,940 B2 | 4/2005 | Potts et al. | |
| 2001/0050083 A1 | 12/2001 | Marchitto et al. | |
| 2004/0023849 A1 | 2/2004 | Robinson et al. | |
| 2006/0015058 A1 | 1/2006 | Kellogg et al. | |
| 2006/0094944 A1 | 5/2006 | Chuang | |
| 2007/0185431 A1 | 8/2007 | Kern | |
| 2007/0269379 A1 | 11/2007 | Mitragotri et al. | |

(Continued)

OTHER PUBLICATIONS

Related Corresponding U.S. Appl. No. 11/733,692, filed Apr. 10, 2007, entitled Iontophoresis Apparatus and Method.

(Continued)

*Primary Examiner* — Jackie Ho
*Assistant Examiner* — Michael J Anderson
(74) *Attorney, Agent, or Firm* — Ropes & Gray LLP

(57) ABSTRACT

An iontophoresis apparatus and method is disclosed that is suited to deliver a plurality of treatment methods such as, but not limited to, body site conductivity enhancement followed by low voltage iontophoresis.

33 Claims, 18 Drawing Sheets

U.S. PATENT DOCUMENTS

2008/0274166 A1* 11/2008 Sacks et al. ................... 424/449
2009/0221951 A1* 9/2009 Nakayama et al. ............. 604/20

OTHER PUBLICATIONS

Related Corresponding Japanese Patent Application JP 2007-230431 filed Sep. 5, 2007, entitled Iontophoresis Apparatus and Method.

Related Corresponding European Patent Application EP 07017514.6 filed Sep. 6, 2007, entitled Iontophoresis Apparatus and Method.

Related Corresponding Japanese Patent Application JP 2007-230413 filed Sep. 56, 2007, entitled Iontophoresis Apparatus and Method.

* cited by examiner

| Body Location | Iontophoretic Treatment | Hours Non-Enhanced | Hours Enhanced | Percent Reduction |
|---|---|---|---|---|
| Arm | Tennis Elbow | 2.1 | 1.5 | 29% |
| Wrist | Carpal Tunnel Syndrome | 4.6 | 2.5 | 46% |
| Knee | Patellar Tendonitis | 5.5 | 1.8 | 67% |
| Average | | 4.1 | 1.9 | 52% |
| St Dev | | 1.8 | 0.5 | 71% |

| Enhancement Period | Treatment Time for 72 milliAmp-minutes |
|---|---|
| 1.2 minutes | 88 minutes |
| 3.0 minutes | 81 minutes |
| 5.0 minutes | 80 minutes |

| Human Ailment | Human Body Site |
|---|---|
| Patella Tendonitis | Patella (also referred to as the "knee" in this disclosure) |
| Tennis Elbow | Elbow (also referred to as the "arm" in this disclosure) |
| Carpal Tunnel Syndrome | Wrist (referred to as the "wrist" in this disclosure) |

FIG. 12

| Body Site: Knee<br>n = 8 Adults | R1: Total Resistance<br>Immediately After<br>Conductivity Enhancement | R2: Total Resistance<br>at the Initiation of<br>Low Voltage Iontophoresis | Ratio<br>R2:R1 |
|---|---|---|---|
| Average | 4.11 kOhms | 6.57 kOhms | 1.61 |
| Standard Deviation | 0.49 kOhms | 1.09 kOhms | N/A |
| Maximum | 4.78 kOhms | 8.20 kOhms | N/A |
| Minimum | 3.45 kOhms | 4.88 kOhms | N/A |

FIG. 13

| Body Site: Arm<br>n = 3 Adults | R1: Total Resistance<br>Immediately After<br>Conductivity Enhancement | R2: Total Resistance<br>at the Initiation of<br>Low Voltage Iontophoresis | Ratio<br>R2:R1 |
|---|---|---|---|
| Average | 2.84 kOhms | 4.35 kOhms | 1.52 |
| Standard Deviation | 0.61 kOhms | 1.15 kOhms | N/A |
| Maximum | 3.46 kOhms | 5.60 kOhms | N/A |
| Minimum | 2.25 kOhms | 3.34 kOhms | N/A |

FIG. 14

| Body Site: Wrist<br>n = 2 Adults | R1: Total Resistance<br>Immediately After<br>Conductivity Enhancement | R2: Total Resistance<br>at the Initiation of<br>Low Voltage Iontophoresis | Ratio<br>R2:R1 |
|---|---|---|---|
| Average | 5.58 kOhms | 8.63 kOhms | 1.55 |
| Standard Deviation | 0.15 kOhms | 1.08 kOhms | N/A |
| Maximum | 5.68 kOhms | 9.39 kOhms | N/A |
| Minimum | 5.47 kOhms | 7.86 kOhms | N/A |

FIG. 15

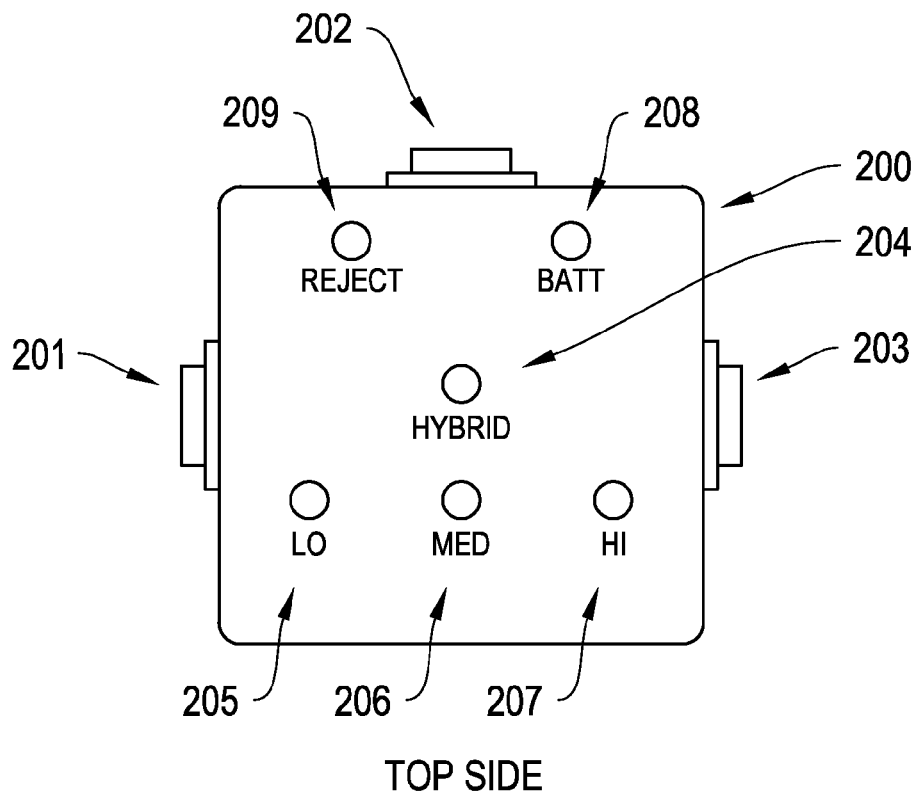
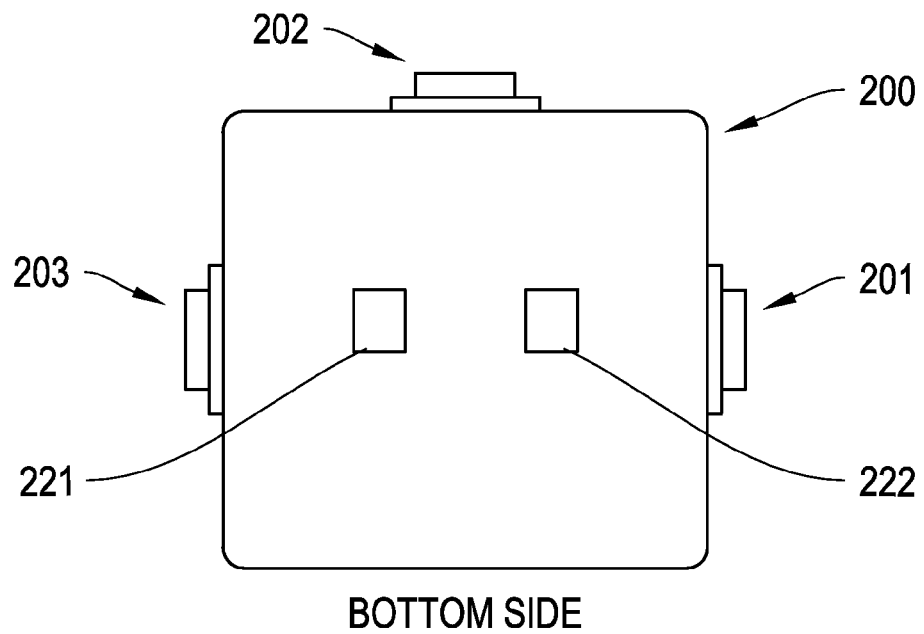
FIG. 17

IONTOPHORESIS APPARATUS AND METHOD

RELATED APPLICATIONS

This application claims the benefit of provisional patent application Ser. No. 60/842,421, filed Sep. 6, 2006, and incorporated herein by reference.

This application is also related to a co-filed U.S. patent application Ser. No. 11/733,692, filed on Apr. 10, 2007, and entitled IONTOPHORESIS APPARATUS AND METHOD.

FIELD OF THE INVENTION

The present invention relates to an iontophoresis apparatus and method that is suited to deliver a plurality of treatments such as, but not limited to, skin conductivity enhancement followed by low voltage iontophoresis.

FEDERALLY SPONSORED RESEARCH OR DEVELOPMENT

None.

BACKGROUND

Iontophoresis drug delivery systems have been commercially available in hospitals and clinics and have also been employed as custom-engineered devices in drug delivery development projects for several decades. However, these systems have many limitations.

A desirable iontophoreis system would include the following attributes: single-use disposable, simple and easy to apply and operate, highly efficient delivery of drug, independent on-board power source, precise on-board electronic dose control, dimensionally small and light weight, comfortable and safe for the patient, and economical to produce and buy. Unfortunately, the reality is that such a device is not currently available.

From a commercial perspective, a practical system might re-use the electronic dose controller instead of disposing of a single-use controller, or deliver a boost of controlled-current dosing instead of relying completely on an on-board patch batteries, or re-charge on-board patch batteries using an external power source, which would be temporarily connected to the patch. Inherent within this kind of practical system would be the need for an economical connection/junction/mounting/switching coupling for receiving external dose control or providing external power source to the patch, while maintaining communication with the fundamental elements of the patch.

SUMMARY OF THE INVENTION

The following is a simplified summary of the invention in order to provide a basic understanding of some aspects of the invention. This summary is not an extensive overview of the invention. It is not intended to identify key or critical elements of the invention or to delineate the scope of the invention. The following merely presents some concepts of the invention in a simplified form as a prelude to the more detailed description provided below.

An illustrative aspect of the invention is directed to a combinational iontophoretic transdermal device that employs both the functionality of a traditional iontophoretic transdermal system and a low voltage iontophoretic transdermal system. In an embodiment in accordance with the present invention, the device can be used for forward iontophoresis (e.g., drug delivery) and/or reverse iontophoresis (e.g., analyte extraction). When employed as a combinational device, the device capitalizes on the advantages of both the traditional system and the low voltage system, while reducing or eliminating disadvantages found with traditional systems and with the low voltage systems alone. In addition, the device can be utilized solely as a traditional iontophoretic system or solely as a low voltage iontophoretic transdermal system, thereby providing the user with therapeutic versatility such as, but not limited to, skin conductivity enhancement.

Another illustrative aspect of the invention is directed to a multi-functional component for application to an integrated or partially-integrated iontophoresis electrode patch, which resolves several issues in regard to interfacing the electrode patch with a separate dose controller module, or a separate power supply module, or a separate re-charger module (for re-charging batteries on-board the patch), or a separate data acquisition module, or a combination of any of the aforementioned.

Other embodiments, systems, methods, features, and advantages of the present invention will become apparent to one having ordinary skill in the art upon examination of the following drawings and detailed description. It is intended that all such additional systems, methods, features, and advantages included within this description be within the scope of the present invention, and can be protected by the accompanying claims.

DESCRIPTION OF THE DRAWINGS

The invention may be better understood with reference to the following drawings. The components in the drawings are not necessarily to scale, emphasis instead being placed upon illustrating the principles of the invention. In the drawings, like reference numerals designate corresponding parts throughout.

FIG. 12 is a table depicting human ailments and corresponding body sites for electrical conductivity characteristics;

FIG. 13 is a table depicting the results of testing a human knee for electrical conductivity characteristics;

FIG. 14 is a table depicting the results of testing a human arm for electrical conductivity characteristics;

FIG. 15 is a table depicting the results of testing a human wrist for electrical conductivity characteristics;

FIG. 17 is a plan view and a bottom view of an embodiment of an iontophoretic controller in accordance with the present invention;

DESCRIPTION OF DETAILED EMBODIMENTS

Figures 1, 2:
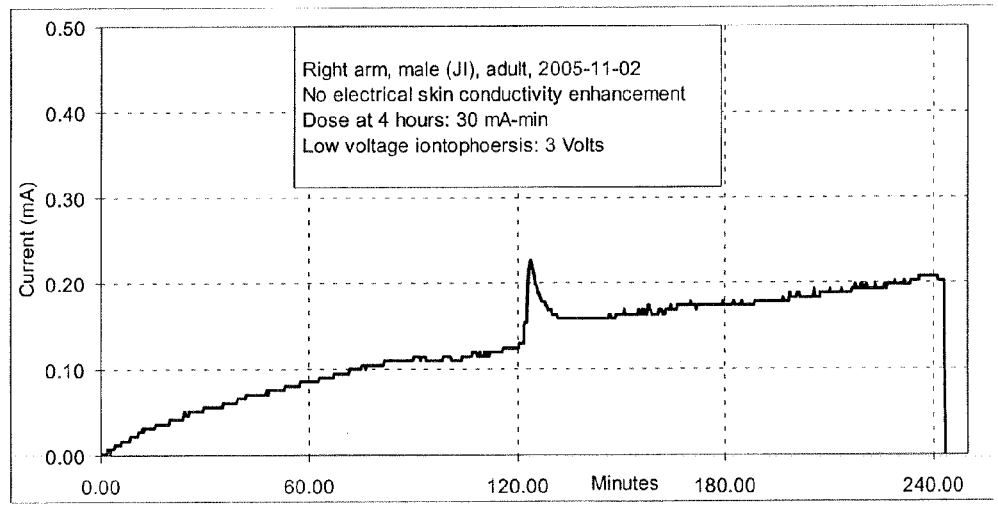
FIG. 1 is a table depicting explanatory data for low voltage iontophoresis at various human body locations, enhanced versus non-enhanced.
FIGS. 2 and 3 are graphs depicting the advantages of electrical skin conductivity enhancement over a period of time wherein, in contrast to FIG. 2, FIG. 3 employs electrical skin conductivity enhancement prior to the low voltage iontophoresis.

The following descriptions of detailed embodiments are for exemplifying the principles and advantages of the inventions claimed herein. They are not to be taken in any way as limitations on the scope of the inventions.

As described herein, in an embodiment, a combinational iontophoretic transdermal device is disclosed that employs the functionality both of a traditional iontophoretic transdermal system and a low voltage iontophoretic transdermal system. The device can be used for forward iontophoresis (e.g., drug delivery) or reverse iontophoresis (e.g., analyte extraction). When employed as a combinational device, the device capitalizes on the advantages of both the traditional systems and the low voltage systems, while reducing or eliminating disadvantages found with the traditional systems and with the low voltage systems. In addition, the device can be utilized solely as a traditional iontophoretic system or solely as a low voltage iontophoretic transdermal system, thereby providing the user with versatility.

As described herein, a methodology is also provided for designing and verifying the operation of combinational iontophoretic transdermal devices. This methodology is preferred because the low voltage iontophoretic operation is open-loop (e.g., minimal electronic control or feedback, minimal electronic current regulation, etc.).

As will be appreciated by those having ordinary skill in the art after studying this disclosure, the inventors have developed a system that monitors, characterized and adapts to changes in skin resistance both before and while delivering a medication to a patient. This is based, at least in part, on the correlation between electrical current and drug delivery. And in particular, wherein electrical conductivity of the patent's skin is enhanced, then the drug delivery rate to the patient is also improved.

In an embodiment, a therapeutic method disclosed herein employs an electronic controller for skin conductivity enhancement (the first phase of this method). The electronic controller has similarities to existing electronic controllers that are used for traditional iontophoresis. The controller is designed to be used for either traditional iontophoresis or in conjunction with the system described herein (i.e., the electronic controller is a multi-option therapeutic device). The skin conductivity enhancement function requires a relatively short period of time (e.g., 2 to 3 minutes).

After skin conductivity enhancement is complete, the electronic controller is removed from the iontophoretic transdermal patch. The remaining portion of the therapy utilizes low voltage. In other words, the second stage of an embodiment of a therapeutic method employs enhanced low voltage iontophoresis. As such, the iontophoretic transdermal patch functions as a traditional iontophoretic patch during skin conductivity enhancement and as a self powered low voltage iontophoretic patch during the remaining portion of the treatment.

The low voltage power source may be embedded within the iontophoretic patch during the manufacturing of the patch, or it can be connected to the patch by the user after the first stage is complete. If it is embedded, then the low voltage source is essentially electrically bypassed during skin conductivity enhancement (i.e., bypassed during the period of time that the patch is powered by the electronic controller). If it is installed after the electronic controller is removed, then it may be connected to the iontophoretic patch using the same connector as that used by the electronic controller.

The present invention provides several advantages over traditional iontophoresis. As known by those having ordinary skill in the art, traditional iontophoresis employs an electronic iontophoretic controller that supplies a relatively high current (e.g., 3 milliAmps). The dose provided is relatively precise. Consider for example an 80 milliAmp-minute treatment at 3 milliAmps. The iontophoretic treatment itself will take approximately 26.7 minutes (26.7 equals 80 milliAmp-minutes divided by 3.0 milliAmps). Add to this the time for preparation, patch application, electrical power ramp-up, electrical power ramp-down, patch removal, cleaning, etc., results in an actual treatment time of about 40 minutes. During this period of time the patient is essentially immobilized (i.e., forced to remain stationary within the clinic), because they are tethered via wire leads to a tabletop or handheld electronic iontophoretic controller and this controller cannot be removed from the clinic. Adding additional time for the waiting period, administrative tasks, etc., results in a total clinic visitation period exceeding one hour. Ideally it would be beneficial, for both the patient and clinician, to reduce this period of time in the clinic.

In contrast, an embodiment of a therapeutic method disclosed herein can have the first stage of therapy conducted in the clinic. This skin conductivity enhancement phase of the treatment requires about 2 or 3 minutes. After this phase the electronic controller is removed. The patient continues to wear the transdermal patch for a few additional hours, but this does not result in immobility because the patient is free to leave the clinic and engage in normal everyday activities. The patch with the associated low voltage power source (which is integral with the patch) is a disposable device, and as such the patient simply removes the patch after a few hours, and then disposes of the patch. Thus, the total clinic visitation period is significantly reduced in comparison to traditional iontophoresis for the same given dosage (e.g., 80 milliAmp-minutes).

As also will be recognized by those having skill in the art, one disadvantage of low voltage iontophoretic transdermal patches is that the average magnitude of delivered current is relatively small. This magnitude is approximately two orders of magnitude lower than that provided by the electronic controllers currently used for traditional iontophoresis. As such, the recommended treatment duration for these low voltage iontophoretic transdermal patches is significant. A typical recommended duration is 24 hours for existing low voltage iontophoretic systems. For example, the IOMED Companion 80 wherein 24 hours is recommended and the Travanti Iontopatch wherein 24 hours is also recommended (Travanti Pharma Inc. was formerly Birch Point Medical Inc).

In contrast, an embodiment of a therapeutic method disclosed herein can have, for example, a typical duration of approximately two hours for the low voltage iontophoretic phase. Accordingly, this represents a significant advantage over the prior-art.

In an embodiment in accordance with the present invention, two stages of operation are employed. The first stage is electrical skin conductivity enhancement. The second stage is an enhanced low voltage iontophoretic transdermal patch treatment.

There are numerous prior-art methods for electrical skin conductivity enhancement. These include, but are not limited to chemical treatment, abrasion, ultrasound, and the use of electrical energy. Traditional electroporation is one example of a common methodology that employs electrical energy for skin conductivity enhancement. Traditional electroporation utilizes high voltage, high energy, and short-duration pulses. In contrast, the present invention does not rely on high voltage and high energy.

Moreover, to minimize circuitry, enhance reliability, and minimize manufacturing costs, an embodiment in accordance with the present invention utilizes the same circuits required for traditional iontophoresis, to implement the skin conductivity enhancement. This circuit function is typically accomplished via an incrementally increased DC voltage with current limitation or an incrementally increased DC current with voltage limitation.

Each embodiment in accordance with the present invention may have differing requirements. For the embodiment described herein the preferred low voltage iontophoretic treatment time will be 4 hours or less. Ideally this low voltage phase will be less than 2 hours on average. This provides a significant and thereby acceptable safety margin because skin resistance, and thus drug transport, varies from patient to patient, or from body site to body site, and there will be a few individuals with high skin resistance, and as such the treatment time will take longer than two hours for these few individuals. As will be appreciated by those having ordinary skill in the art, the invention is not limited to low voltage iontophoretic treatment times having a maximum of 4 hours and preferably less than 2 hours. Accordingly, other times can be used that are greater than 4 hours.

Currently, low voltage iontophoresis (as descried herein) is essentially unregulated. In other words there is no electronic current regulation. Because there is no electronic current regulation the current magnitude will vary for each treatment application.

The magnitude of current during the low voltage phase is dependent on skin resistance. If the skin conductivity is not initially enhanced, then the skin resistance of patients will vary more and will be greater in magnitude. As such the treatment duration will vary significantly, and may be greater than the desired maximum of 4 hours.

Two advantages provided by the electrical skin conductivity enhancement stage of the invention are: 1) significantly reduced time required for low voltage iontophoresis; and 2) significantly reduced variance in time require for different body sites (i.e., there is essentially a normalization of skin conductivity).

The table in FIG. 1 provides explanatory data for low voltage iontophoresis (80 milliAmp-minutes, 6 Volt nominal low voltage iontophoresis, female adult).

In a first embodiment in accordance with the present invention, the transdermal system is iontophoretically effective for at least 3 different body sites. These sites include the arm, wrist, and knee. The system can also be iontophoretically effective for other body sites having similar electrical conductivity characteristics in comparison to these 3 body sites.

The table in FIG. 1 displays treatment durations for a 6 Volt low voltage iontophoretic system that does not employ electrical skin conductivity enhancement ("Hours Non-Enhanced"). The treatment duration for the 3 body sites varies from a minimum of 2.1 hours (for the arm) to a maximum of 5.5 hours (for the knee). The range in duration is significant and the longer durations of 4.6 hours (for the wrist) and 5.5 hours (for the knee) are undesirable. The average treatment duration is 4.1+/−1.85 hours (+/− one standard deviation).

The table in FIG. 1 also displays treatment durations for a 6 Volt low voltage iontophoretic system that does employ electrical skin conductivity enhancement ("Hours Enhanced"). The treatment time for all three body sites is significantly reduced (all three are 2.5 hours or less). All three periods are relatively similar (i.e., there has been some level of electrical conductivity normalization, which has provided some level of treatment time duration normalization). The average treatment duration is 1.9+/−0.5 hours (+/− one standard deviation). All three treatment durations are approximately equal to a desired period of 2 hours, which meets the design requirements for the first embodiment in accordance with the present invention as it applies to providing conductivity enhancement for low voltage iontophoresis.

Figure 3:
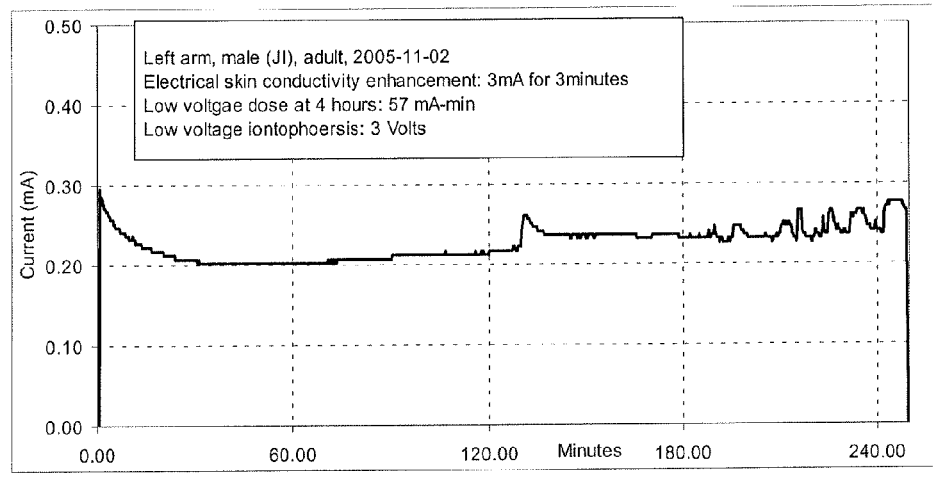

The graphs of FIG. 2 and FIG. 3 illustrate the advantage of electrical skin conductivity enhancement with the magnitude of current for a low voltage iontophoretic system employing 3 Volts. The treatment represented by FIG. 2 does not employ electrical skin conductivity enhancement prior to the low voltage iontophoresis. As such, the improvement in skin conductivity occurs slowly over the entire 4 hour period, which results in a reduction of average current, which in turn results in the relatively lower overall dose of 30 milliAmp-minutes.

The treatment represented by FIG. 3 does employ electrical skin conductivity enhancement prior to the low voltage iontophoresis. As such, the skin conductivity is maximized from the very beginning of treatment (indicated by the relatively high level of current at the beginning of treatment), which in turn facilitates relatively high average current for the entire 4 hour period, which in turn results in the relatively higher overall dose of 57 milliAmp-minutes (an approximate 2:1 improvement).

In FIG. 2, there is a spike in current at the elapsed time of 125 minutes. This is probably due to arm movement, which in turn alters the interface between the skin and each electrode. Such perturbations are common because the low voltage iontophoretic electrical operation is essentially open loop.

Typically, the treatment duration for low voltage iontophoretic devices (e.g., the IOMED Companion 80) is primarily dependent on skin resistance because these devices do not employ electronic current regulation. As such, a treatment at one body site (e.g., the knee) may require 200% to 400% the time duration in comparison to a treatment on another body site (e.g., arm) for an equal dose (e.g., 80 milliAmp-minutes). In addition, the treatment duration may vary for the same body site on different days (because skin resistance for a given body site varies with respect to health, humidity, temperature, time of day, etc). In addition, the treatment duration may vary for the same body site on different people, due to differing skin characteristics.

Thus, skin resistance creates many problems for low voltage iontophoretic devices. Typical problems include: 1) incomplete dose of drug delivery achieved within the recommended patch wear period; 2) significant variance in treatment time for the same body site on different people; and, 3) significant variance in treatment time for different body sites on the same human body. Some of the advantages of the invention disclosed herein are the correction of these three specific problems and similar resistance related problems.

Figure 4:
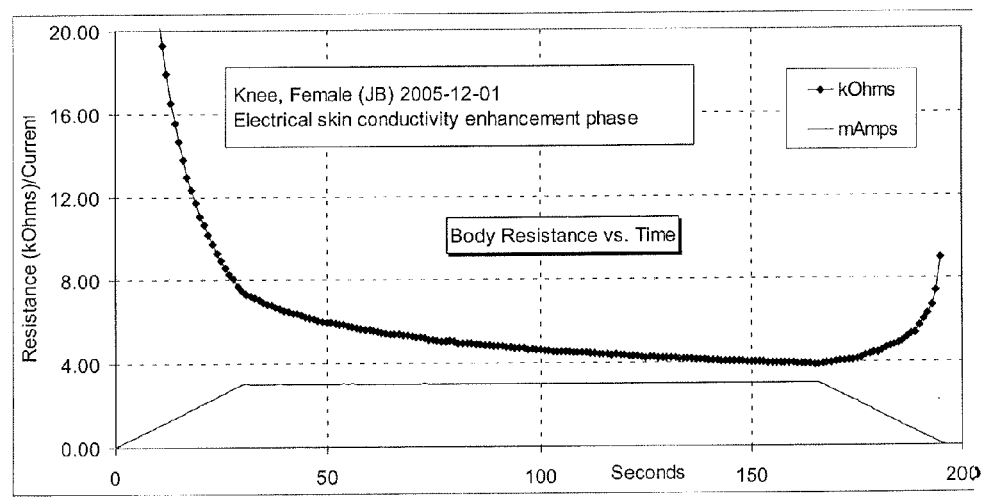
FIG. 4 is a graph depicting the reduction and trend toward normalization of skin resistance during an electrical skin conductivity enhancement phase.

The reduction and approximate normalization of skin resistance during the electrical skin conductivity enhancement phase is illustrated in FIG. 4. As will be appreciated by those having ordinary skill in the art, resistance is inversely proportional to conductivity. Thus, a decrease in resistance translates to an increase in conductivity (i.e., enhancement in electrical conductivity, and potential drug flux). The units for resistance are Ohms and the units for conductivity are Mhos (or 1/Ohms).

The initial skin resistance is relatively large: 270 kOhms at 0.025 milliAmp (off the graph). It falls to 7.5 kOhms when the current reaches 3.0 milliAmp (30 seconds elapsed). It continues to drop during the constant current state, dropping to a minimum of 3.87 kOhms just prior to current ramp-down (current ramp-down in initiated at 166 seconds elapsed). As shown, during current ramp-down the resistance increases (i.e., a percentage of the enhanced conductivity is lost before the enhancement phase is complete). Conductive pathways in the skin are "re-healing" as the magnitude of current decreases. A specific resistance measurement is acquired when the voltage decreases to approximately 6 Volts. In an embodiment in accordance with the present invention, this measurement at 6 Volts is used to calculate the approximate resistance that will exist during the subsequent low voltage iontophoresis phase (which employs a 6 Volt potential).

Figure 5:
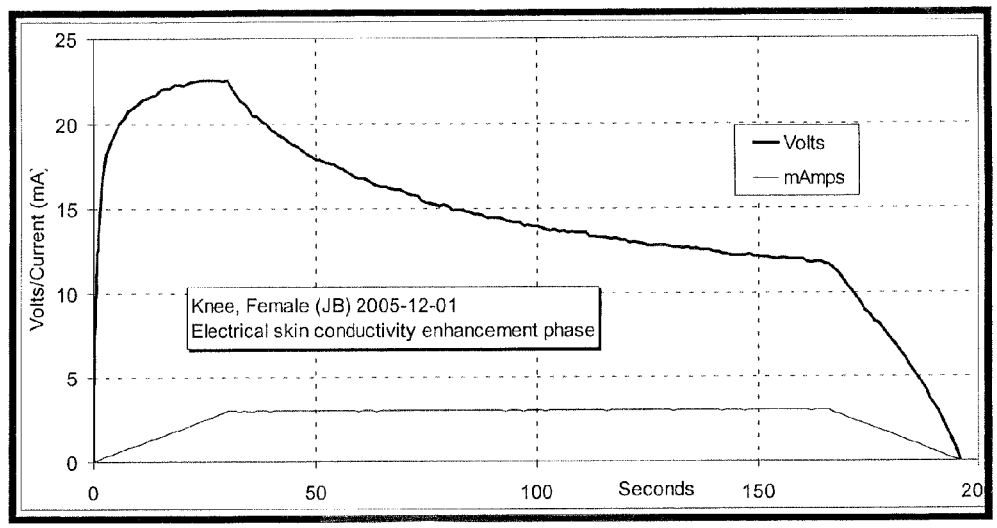
FIG. 5 is a graph illustrating the voltage and current, over time, corresponding to the pre-conductivity enhancement phase of FIG. 4.

FIG. 5 illustrates the voltage and current that corresponds to FIG. 4. As shown, the voltage drops to 6 Volts at the approximate elapsed time of 183 seconds. Accordingly, this is the time when the specific resistance measurement is acquired. For sake of explanation this measurement is named "R1".

In a prototype of the first embodiment in accordance with the present invention, empirical test methods were utilized to calculate the ratio of the low voltage iontophoresis resistance (i.e., the resistance that exists during subsequent low voltage iontophoresis phase) to the resistance measured during the last few seconds of the electrical skin conductivity enhancement phase. The table in FIG. 13 indicates a ratio 1.61:1 for the knee based on a sample size of 8 adults. The standard deviation is relatively low and as such this calculation can be used to obtain an acceptable "ball-park" or estimated computation.

In one embodiment, this resistance calculation may be used by the electronic circuitry to calculate the approximate time for the subsequent low voltage iontophoresis phase. For example, if the "R1" measurement yields 4.0 kOhms, then the approximate resistance for the low voltage iontophoresis will be 6.44 kOhms (1.61×4.0 kOhms). The typical voltage potential for the low voltage iontophoresis phase is 5.5 Volts for 6.44 kOhms, which yields 0.85 milliAmps per Ohms Law. This in turn yields an 85 minute treatment (85 minutes=72 milliAmp-minutes/0.85 milliAmps). The remaining treatment time may be displayed on a LCD or other type of display.

In another embodiment, this time calculation may be used to verify that the low voltage iontophoresis treatment will be complete within a specified maximum treatment time period, e.g., within 4 hours. If the time exceeds the maximum limit then an appropriate warning can be issued to the clinician and/or patient during the electrical skin conductivity enhancement phase.

To simplify this warning concept it is not necessary to calculate the low voltage iontophoresis treatment time period, because the time period is proportional to resistance "R1", i.e., it is only necessary to calculate "R1".

Likewise, the calculation can be further simplified by simply evaluating the magnitude of current at a particular voltage (which per Ohm's Law is proportional to resistance). For example, consider an application wherein the knee is to be treated with a dose requirement of 72 milliAmp-minutes within a maximum treatment duration of 4 hours. This equates to 0.3 milliAmp-minutes per minute, and this equates to 0.3 milliAmps minimum average current. With a typical voltage potential of 6 Volts, this yields a maximum low voltage iontophoresis resistance of 20 kOhms (R=V/I). According to the table within FIG. 13, the R2:R1 ratio is 1.61 for the knee. Therefore, R1=12.4 kOhm (20/1.61). The current for 6 Volts at 12.4 kOhms is 0.49 milliAmps (I=V/R). Thus, near the end of the electrical skin conductivity enhancement phase the electronic controller can verify that the current measurement at 6 Volts is 0.49 milliAmps or greater. If the current is less than 0.49 milliAmps then the user is warned accordingly (via flashing LEDs or via an annunciator warning sequence or the like.) In a model of the first embodiment in accordance with the present invention, a microcontroller was employed with very limited mathematical computing capability. As such, this simplest calculation method was employed.

In another embodiment, the current measurement is acquired after the electrical skin conductivity enhancement phase. Within a finite period after the current is ramped down to zero, e.g., five seconds, the voltage is set to a magnitude approximately equal to the voltage potential utilized for low voltage iontophoresis, e.g., 6 Volts, and the current is measured. This methodology has the advantage of minimizing or eliminating the R2:R1 ratio described previously, thereby simplifying and/or improving the calculation.

In the model of the first embodiment in accordance with the present invention, numerous measurements (i.e., not one single "R1" related measurement) were acquired by a microcontroller approximately every millisecond, for several milliseconds, and then averaged to reduce noise and improve the accuracy of the measurement.

In another embodiment, the "R1" related measurement can be used to test for excessive electrical conductivity, where this high level of conductivity is related to damaged skin (e.g., a break in the skin) or other abnormality.

Referring again to FIG. 4, the rate in change in resistance decreases with time. Eventually the resistance will reach a minimum and no longer change with time. As such, the change in resistance (i.e., the first derivative of resistance) can be utilized as a method of determining when to terminate the electrical skin conductivity enhancement phase.

Desirably, the second stage low voltage iontophoretic voltage potential is optimized to the level of electrical skin conductivity enhancement as required to take full advantage of the increased level of electrical skin conductivity achieved during electrical skin conductivity enhancement.

Figure 6:
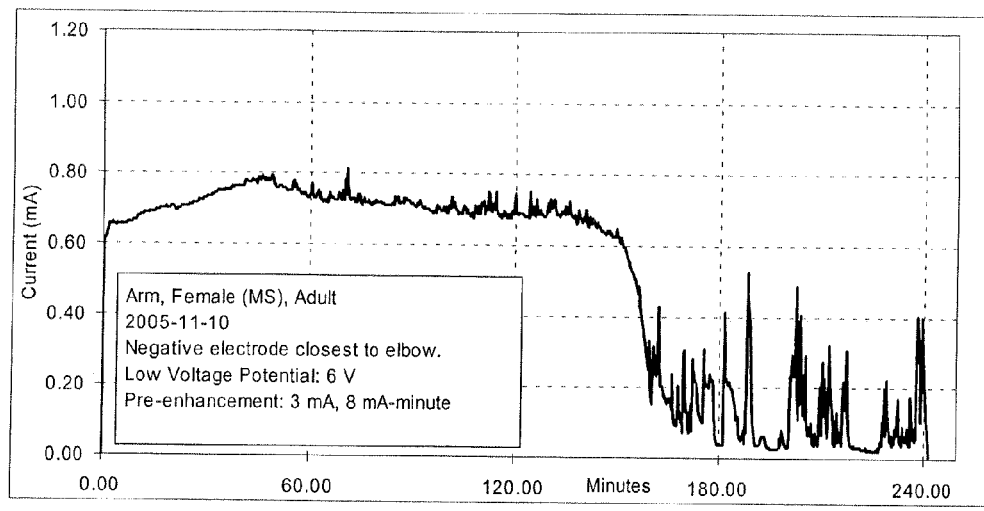
FIG. 6 is a graph illustrating a low voltage treatment wherein optimization has been achieved.

FIG. 6 illustrates a low voltage treatment wherein optimization was achieved for this embodiment. The electrical skin conductivity enhancement phase employed 3 milliAmps and 8 milliAmp-minutes (durations approximately 3 minutes). The illustrated low voltage iontophoresis phase employs 6 Volts nominal, and a 72 milliAmp-minute dose is achieved in 100 minutes (well below 240 minute requirement).

The optimization can be observed by the fact that the current remains relatively constant from the onset and for the entire treatment. In other words, the voltage potential utilized during the low voltage iontophoresis phase is sufficient to sustain, or enhance, the increased level of electrical conductivity provided by the electrical skin conductivity enhancement whereas without enhancement, current starts much lower and is often slowly rising throughout treatment.

In FIG. 6, the current is effectively turned-off at the elapsed time of 160 minutes. The iontophoretic patches employed in a model of the first embodiment in accordance with the present invention include a conventional electrochemical overdose limitation switch that terminates the treatment at some finite dose after the 80 milliAmp-minutes is achieved. For this particular iontophoretic patch the overdose limitation switch effectively terminated the current at about 121 milliAmp-minutes at the approximate elapsed time of 160 minutes.

Figure 7:
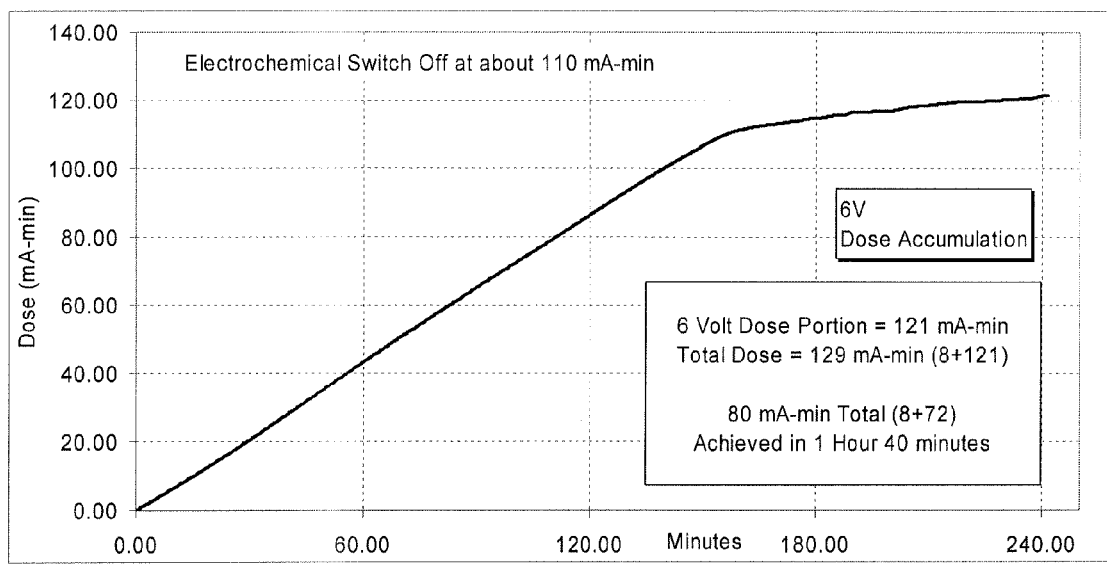
FIG. 7 is a graph illustrating the dose accumulation for the current delivered in FIG. 6.

In FIG. 6, the low voltage iontophoretic dose of 72 milliAmp-minutes in addition to the 8 milliAmp-minutes dose achieved during the electrical skin conductivity enhancement phase results in the minimum required patient iontophoretic dose of 80 milliAmp-minutes within 2 hours. Moreover, FIG. 7 illustrates the dose accumulation (i.e., charge in units of milliamp-minutes) for the current delivered as illustrated in FIG. 6. In FIG. 7, 72 milliAmp-minutes is achieved in approximately 100 minutes (i.e., 1.67 hours). As such, the treatments was completed within 2 hours (i.e., 120 minutes), well within the desired 240 minute requirement.

Figure 8:
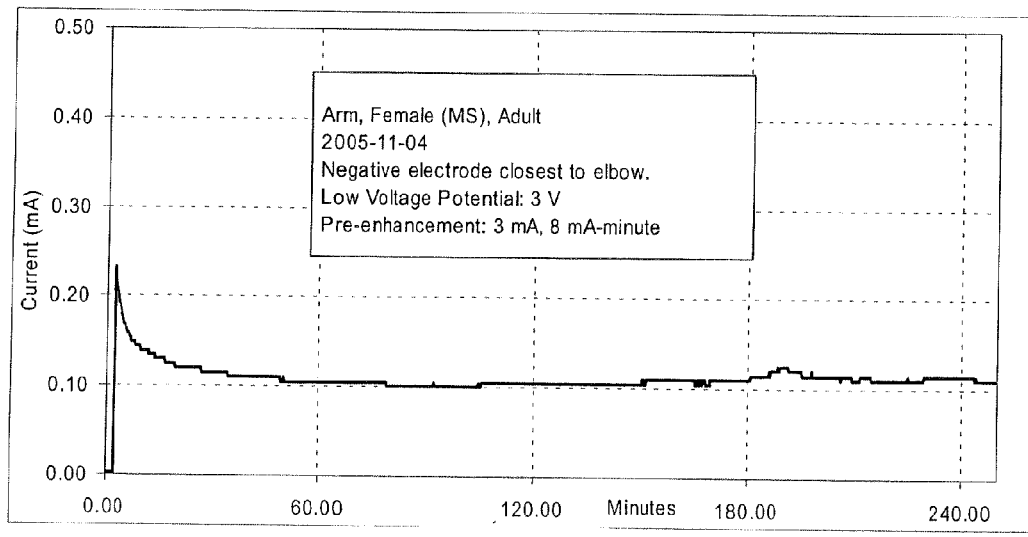
FIG. 8 is a graph illustrating an iontophoresis treatment wherein optimization has not been achieved.

FIG. 8 illustrates a treatment wherein optimization was not achieved for this type of embodiment. Like the treatment associated with FIG. 6, the electrical skin conductivity enhancement phase employed 3 milliAmps and 8 milliAmp-minutes. Unlike the treatment associated with FIG. 6, the low voltage iontophoretic employed 3 Volts in lieu of 6 Volts. As a result, the required 72 milliAmp-minutes dose was not achieved within the 240 minute (4 hour) requirement. After 240 minutes the dose achieved during the low voltage phase was approximately 53 milliAmp-minutes.

The lack of optimization can be observed by the fact that current initially decreases. Within the first hour the current decreased from about 0.23 milliAmps to 0.10 milliAmps. The current decreased to 43% of the initial magnitude. Therefore, the resistance increased 230% (i.e., the electrical conductivity decreased to 43% of the initial value.) This increase in resistance indicates that the 3 Volt potential is inadequate to sustain the enhanced level of skin electrical conductivity provided during the electrical skin conductivity enhancement phase. As such, the low voltage iontophoresis voltage magnitude is not optimized to the level of electrical skin conductivity enhancement.

Desirably, the operation of the electrical skin conductivity enhancement phase (i.e., first phase) is optimized for the low voltage iontophoresis phase (i.e., second phase) as required to maximize electrical skin conductivity during the low voltage iontophoretic stage. Accordingly, shown in FIG. 10, during the electrical skin conductivity enhancement phase, less time is insufficient for enhancing conductivity and more time fails to provides a significant increase in conductivity.

Consider an example with the following specifications: total treatment time of 4 hours or less, typical treatment time of 2 hours, current density of 0.53 milliAmps/(centimeters$^2$) or less for electrical skin conductivity enhancement, and electrical skin conductivity enhancement period of 5 minutes or less.

The parameters that dictate the effectiveness of the electrical skin conductivity enhancement are primarily current density and time. In a model for this embodiment, both the area of the anode electrode and area of the cathode electrode were the same and are equal to 5.71 centimeters$^2$. Therefore, the maximum current density of 0.53 milliAmp/(centimeters$^2$) corresponds to a maximum current magnitude of 3.0 milliAmps.

The resultant parameters for this embodiment are determined and verified empirically. Initially the electrical skin conductivity enhancement is established at 3.0 milliAmp (the allowed maximum). For this example electrical skin conductivity enhancement periods of 1, 3, and 5 minutes were tested in conjunction with low voltage iontophoretic voltage potentials of 3 Volts and 6 Volts (corresponding to one lithium battery cell and two series connected lithium battery cells).

Figure 9:
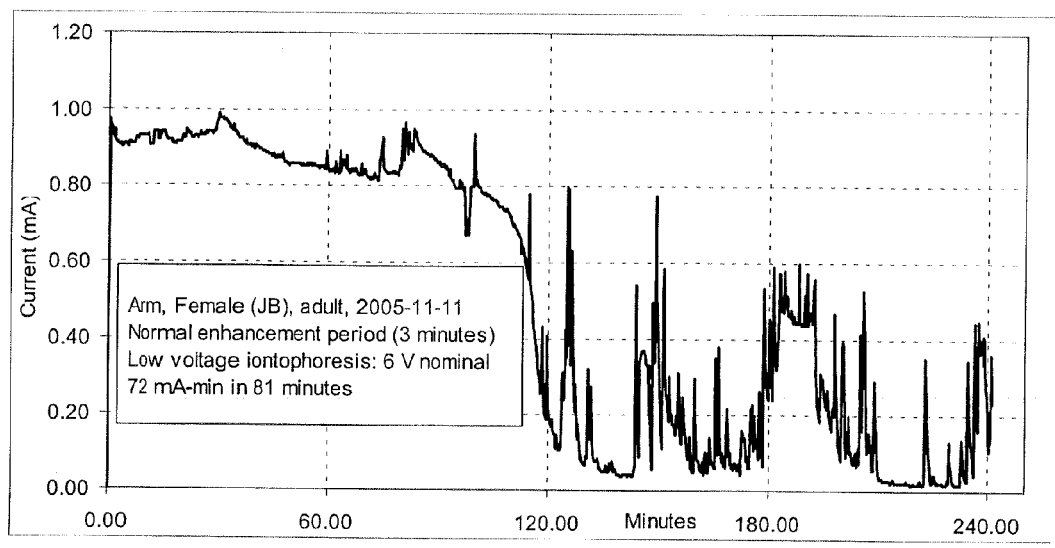
FIG. 9 is a graph illustrating the achievement of optimization wherein the magnitude of current remains fairly constant during the entire low voltage iontophoresis stage until the dose limitation switch results in a decrease in current at approximately 100 minutes.

FIG. 9 illustrates the achievement of optimization (because the magnitude of current remains fairly constant during the entire low voltage iontophoresis stage until the dose limitation switch results in a decrease in current at approximately 100 minutes).

The low voltage iontophoresis stage employs 6 Volts of nominal potential. The electrical skin conductivity enhancement phase employs 3 milliAmps for a duration of 3 minutes.

Testing verified that a low voltage iontophoretic stage employing 3 Volts nominal was unacceptable (i.e., typical duration was significantly greater than the required two hours) regardless of the length of the electrical skin conductivity enhancement duration. Therefore, the need for 6 Volts was verified.

Further testing was conducted to determine the optimum period for the electrical skin conductivity enhancement based on 6 Volts for low voltage iontophoresis. The results are provided in the table in FIG. 10. Note that lengthening the period beyond 3 minutes resulted in no significant improvement.

Moreover, there is a significant difference between the 3 minute period and 1.2 minute period, which indicates 1.2 minutes is somewhat insufficient. As such, the optimum period lies between 1.2 and 3.0 minutes, and as such further empirical testing may be conducted if further optimization is deemed necessary. For this example, i.e., for the model of the first embodiment in accordance with the present invention, it was not deemed necessary, and as such the three minute enhancement period was established.

Figures 10, 11:
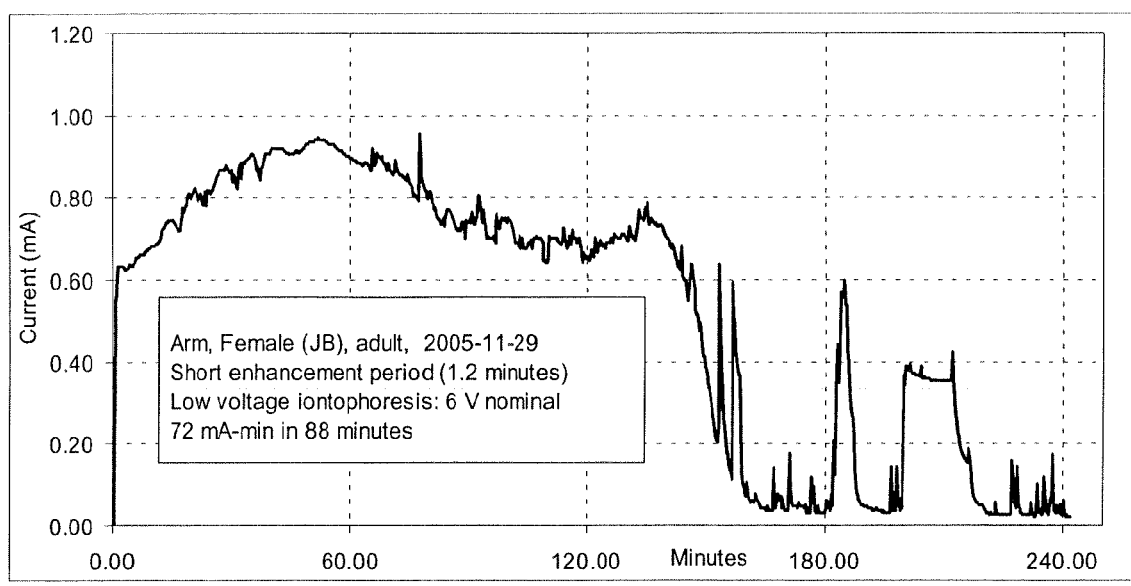
FIG. 10 is a table depicting testing results conducted to determine the optimum period for electrical skin conductivity enhancement based on 6 Volts for low voltage iontophoresis.
FIG. 11 is a graph illustrating lack of optimization that occurs with insufficient conductivity enhancement.

FIG. 11 illustrates lack of optimization that occurs with insufficient conductivity enhancement. Note that during the first hour of low voltage iontophoresis current increases substantially which indicates that there was insufficient electrical skin conductivity enhancement. This insufficiency is due to either insufficient time or insufficient current density or a combination thereof. In this example it is due to the insufficient period of time (i.e., only 1.2 minutes), given the fact that the current density of 0.53 milliAmp/(centimeters$^2$) is the maximum allowed for this particular example.

During the design of a device in accordance with the present invention, the body site (or sites) to be treated must be considered. For this example, i.e., for the first embodiment of this invention, the specification desired that the model be utilized for three body sites, or any other body site, which has equal or better electrical conductivity characteristics. The sites for the model are indicated in the table provided by FIG. 12. Accordingly, testing was conducted at each of these body sites on several different adults.

Initially the knee of eight adults was tested (six females, two males). The results are provided in the table provided by FIG. 13. Note that total resistance is primarily the sum of the subdermal body resistance, skin resistance at the anode electrode, skin resistance at the cathode electrode, anode electrode resistance, and cathode electrode resistance. For this example, and most iontophoretic drug delivery applications, the skin resistances contribute to about 95% of the total resistance.

Referring to the table provided by FIG. 13, after the 3 minute, 3 milliAmp electrical skin conductivity enhancement phase, the average total resistance was 4.11+/−0.49 kOhms (+/− one standard deviation) at approximately 6.0 Volts. (The resistance is measured at a specific voltage because skin resistance is nonlinear and inversely proportional to current and therefore inversely proportional to voltage). The ration R2:R1 is used to calculate the approximate resistance for the subsequent low voltage iontophoresis phase.

The table within FIG. 14 is for the arm and the table in FIG. 15 is for the wrist. The R1:R2 ratios are similar for all three different body sites (1.61:1 for the knee, 1.52:1 for the arm, and 1.55:1 for the wrist). As such, an average of the three can be used as a "universal constant" by a microcomputer (or the like) within the electronic skin conductivity enhancement device in accordance with the present invention. This constant can be used to calculate the low voltage iontophoresis time period, or determine if the resistance is acceptable for low voltage iontophoresis (i.e., below an acceptable upper limit as required to guarantee treatment completes within a given time period, e.g., 4 hours). In another embodiment the worse-case ratio could be utilized, to ensure the correct operation of all body sites.

Figure 16:
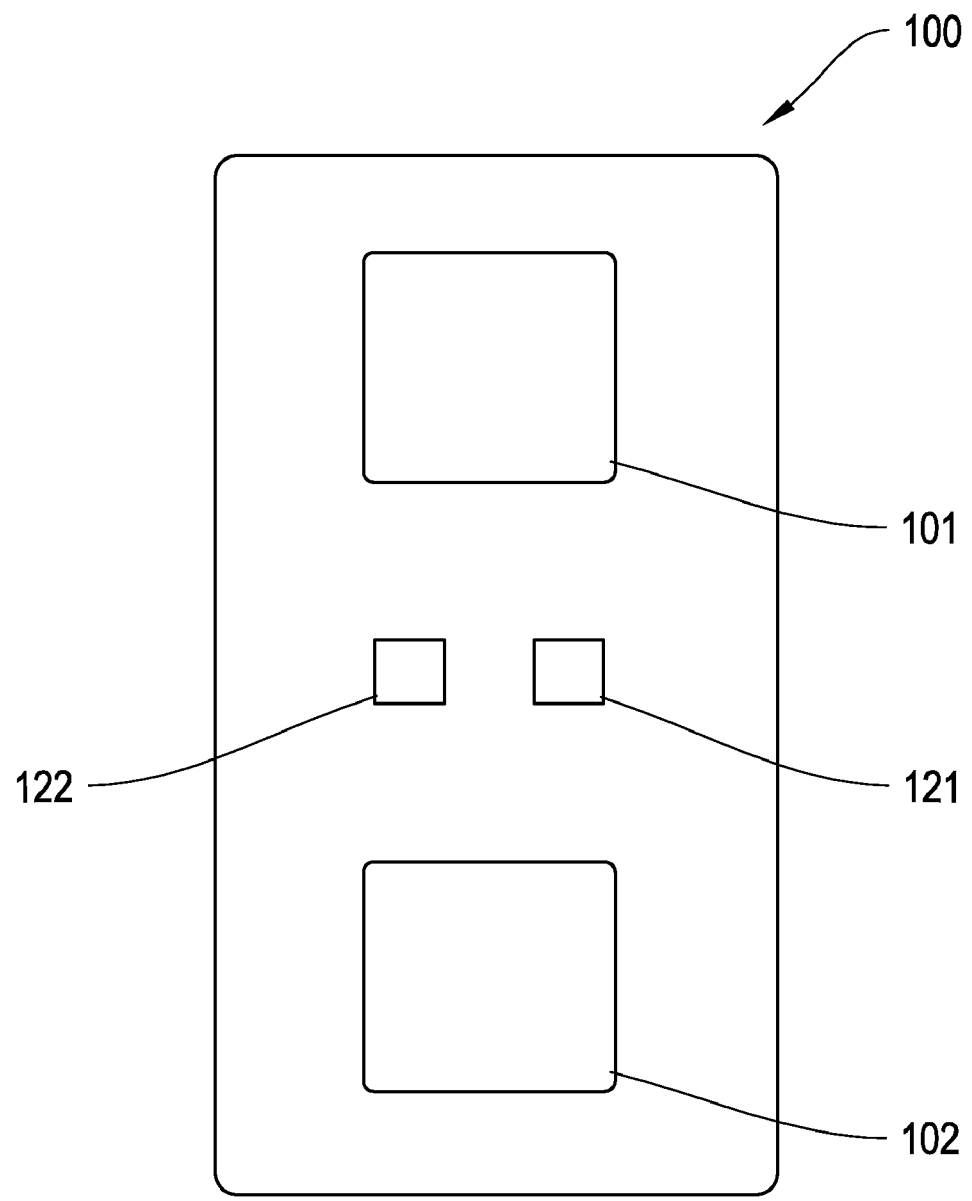
FIG. 16 is a plan view of an embodiment of an iontophoretic patch in accordance with the present invention.
Figure 18:
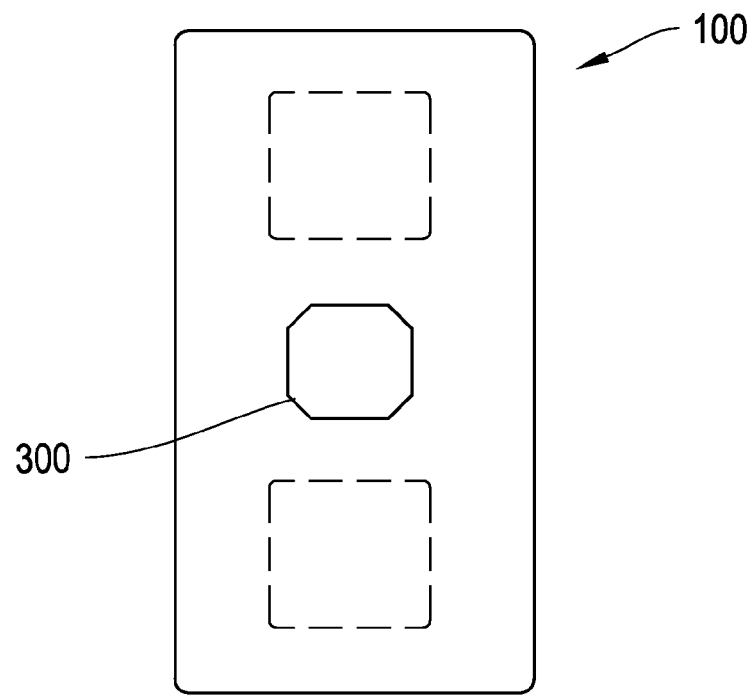
FIG. 18 is a plan view of an embodiment of a low voltage battery pack in accordance with the present invention.
Figure 19:
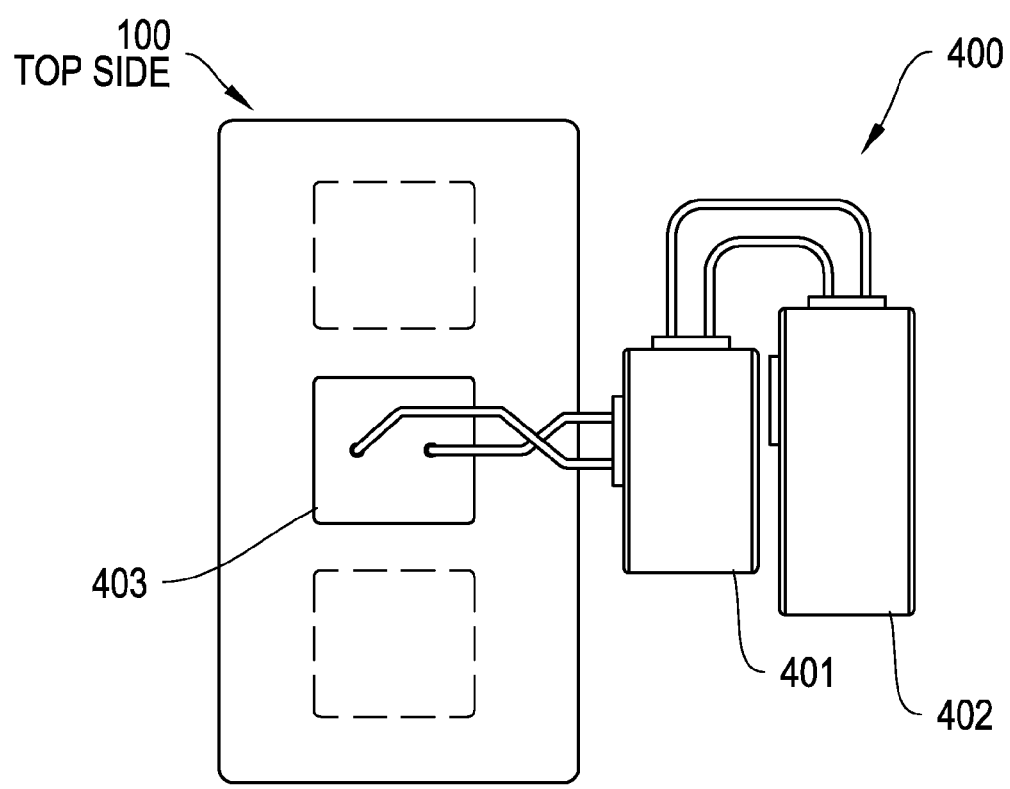
FIG. 19 is a plan view of an embodiment of a data logging system in accordance with the present invention and attached to the patch of FIG. 16.

The following explanation applies to one embodiment in accordance with the present invention. However, it should be noted that the invention is not limited to this one embodiment. In the FIGURES: FIG. 16 depicts an iontophoretic patch; FIG. 17 depicts an electronic iontophoretic controller in accordance with the present invention; FIG. 18 depicts a low voltage battery pack; and, FIG. 19 depicts a data logging system attached to the iontophoretic patch.

In FIG. 17, the iontophoretic controller 200 can be setup for either traditional iontophoresis or for electrical skin conductivity enhancement (i.e., hybrid mode). The first time the ON-Select Pushbutton 201 is depressed the device turns on and hybrid mode is selected. This is indicated via the Hybrid LED 204. Pressing the On-Select Pushbutton a second time transfers the device to the first of the three traditional iontophoresis modes, which is the Low Current Mode. This is indicated via the Low LED 205. Pressing the On-Select Pushbutton a third time transfers the device to the second of the three traditional iontophoresis modes, which is the Medium Current Mode. This is indicated via the Medium LED 206. Pressing the On-Select Pushbutton a fourth time transfers the device to the third of the three traditional iontophoresis modes, which is the High Current Mode. This is indicated via the High LED 207. Pressing the On-Select Pushbutton a fifth time restarts the selection process, in other words the device transfers back to the hybrid mode. This is indicated via the Hybrid LED 204.

The Low Current Mode may correspond to 2 milliAmps, or any low level current. The Medium Current Mode may correspond to 3 milliAmps, or any middle level current. The High Current Mode may correspond to 4 milliAmps, or any high level current.

A yellow Battery Warning LED 208 is provided to indicate battery status. The model of the first embodiment of this invention employs a rechargeable battery. Another embodiment can employ a primary battery or other suitable power source.

A red Electrode Reject LED 209 is provided to indicate operational errors (e.g., discontinuity of current).

To setup the controller for traditional iontophoresis the user turns on the device using the ON-Select Pushbutton 201 and selects Low, Medium, or High using the ON-Select Pushbutton. The dose is preferably fixed at 40 milliAmp-minutes. The controller 200 is attached to the iontophoretic patch 100 of FIG. 16. The iontophoretic patch 100 is applied to the body. The user starts the traditional iontophoresis treatment by depressing the Start Pushbutton 202. At the end of the treatment the device may sound an audio annunciator to provide an indication of treatment complete and the controller may turn off automatically.

Alternatively, the user can prematurely terminate a traditional iontophoresis treatment before it is complete by pressing the Off Pushbutton 203. After the traditional iontophoresis treatment is complete the iontophoretic patch 100 and controller 200 are removed.

Referring to the iontophoretic patch 100 of FIG. 16, the controller 200 of FIG. 17 connects to the iontophoretic patch 100 via two electrical connection points on the patch 121, 122. For example controller connection node 221 connects to patch connection node 121 and controller connection node 222 connects to patch connection node 122. Connection point 121 connects to one of the two electrodes (either the anode or cathode). Assume 121 connects to the cathode 101, then 122 connects to the anode 102. These connections may be direct or may be via an electrical circuit component (e.g., current limiting resistor).

The iontophoretic patch 100 is specifically designed to mate with the controller 200. In one embodiment, one type of iontophoretic patch 100 can be designed to be used for both traditional iontophoresis, electrical skin conductivity enhancement and low voltage treatments. In another embodiment there can be one iontophoretic patch specifically designed for traditional iontophoresis and different iontophoretic patches designed for electrical skin conductivity enhancement and the subsequent low voltage iontophoresis that immediately follows enhancement.

As indicated herein it is desirable to evaluate the electrical parameters of the low voltage iontophoresis system, as part of the design and verification processes. Accordingly, an external measurement system, i.e., data logging system 400 of FIG. 19 can be used.

The following explanation applies to one method of using an embodiment in accordance with the present invention for traditional iontophoresis. Initially, the iontophoretic patch 100 is placed on the body site to be treated. Next, the iontophoretic controller 200 is setup for one of the three currents magnitude (this is dependent on patient tolerance). Next, the iontophoretic controller 200 is connected to the iontophoretic patch 100 body site to be treated. Next the iontophoretic controller 200 is started. Operation of the device in the traditional iontophoresis mode is synonymous with prior-art electronic iontophoretic controllers. Because the electronic iontophoretic controller 200 employs an electronic current regulator the current delivered is relatively precise and therefore the period of time required is relatively precise.

The following explanation applies to one method of using an embodiment in accordance with the present invention for electrical skin conductivity enhancement. Initially the iontophoretic patch 100 is connected to the body. Next, the iontophoretic controller 200 is setup for electrical skin conductivity enhancement mode (i.e., hybrid mode). Next, the iontophoretic patch 100 is placed on the body site to be treated. Next, the iontophoretic controller 200 is started. Operation of the device is analogous to an abbreviated traditional iontophoresis treatment. For example the embodiment described herein employs an 8 milliAmp-minute treatment at 3 milliAmps. This requires about three minutes. After this abbreviated regulated current treatment is complete, the electronic iontophoretic controller 200 may beep and turn off automatically, and then will be removed from the low voltage iontophoretic patch 100. The low voltage power source 300 (FIG. 18) is connected to iontophoretic patch 100. The low voltage iontophoretic patch 100 and power source 300 remain connected to the body site for a few hours. After the treatment, the iontophoretic patch 100 and power source 300 are removed and disposed of.

In another embodiment, the power source 300 is an integral component of the iontophoretic patch 100. After the electrical skin conductivity enhancement phase is complete, the electronic controller 200 is removed. Upon removal of the controller 200, the integral power source 300 is connected to the anode and cathode as required to supply the low voltage required for the low iontophoresis phase of the treatment. The electrical connection of the power source 300 may be automatic or manual, or a combination thereof. The automatic connection may be mechanical, electronic (e.g., transistor switch), electromechanical, or the like.

In certain cases the electrical skin conductivity cannot be enhanced. For example, if the patch is connected to the bottom of a foot, the resistance will be relatively high (i.e., the electrical conductivity will be relatively low). Empirical testing conducted for this disclosure indicates a resistance of approximately 40 kOhms at 6 Volts for the bottom of the foot at the conclusion of a 3 minute electrical skin conductivity enhancement phase. As indicated herein, the electronic circuitry detects this high resistance. In accordance with the first embodiment, an associated warning can be provided. This warns the user that the subsequent low voltage iontophoresis treatment should not be initiated. For this scenario the user has the option to continue the treatment using the traditional iontophoretic capabilities of the device.

As will be appreciated by those having ordinary skill in the art, the iontophoretic patch 100 in combination with the low voltage power source 300 can be used independently (i.e., without the electronic controller, i.e., without electrical skin conductivity enhancement) to yield another option for the end-user.

In an embodiment, an iontophoretic transdermal process can be applied to a body site in various ways. Accordingly, one can perform traditional or integrated iontophoresis, or any combination thereof with one system.

As disclosed herein, skin resistance is lowered by exposure to higher voltages, and thus skin resistance can initially be lowered with a traditional "punch-through" for approximately 1-5 minutes. After punch-through, treatment may proceed with a more efficient integrated iontophoresis treatment. The subsequent integrated treatment could be battery powered, or it could be unpowered passive delivery through skin with lowered resistance. As used herein, the phrase "punch-through" refers to electrical conductivity enhancement of the skin.

A completely traditional treatment can be performed with the system disclosed herein by extending the "punch-through" treatment time to fulfill a desire complete dose. Conversely, a completely integrated treatment can be performed with the system by not performing the initial "punch-through" treatment at all, and going straight to a battery operated patch.

As will be appreciated by those having ordinary skill in the art, dose controllers control current, monitor voltage and calculate the accumulated iontophoresis dose in milliAmp-minutes. They also are capable of calculating total skin resistance using: $R=V/I$, where R=resistance, V=voltage, and I=current.

The effectiveness of the "punch-through" mode on lowering the skin resistance can be evaluated by comparing the skin resistance calculations as a function of time, i.e. performing the above calculations at different time intervals and comparing their magnitudes.

FIG. 5 is a graph of a punch-through mode where the current is ramped up from zero to 3 mA, and then is maintained at 3 mA for approximately 2.5 minutes before ramping down. In the figure, the voltage gradually decreases as the current is held constant. This is indicative of the resistance (V/I) gradually decreasing over time.

In one embodiment in accordance with the present invention, a hybrid treatment is applied comprising, first, performing the punch-through treatment using a traditional current controlled dose controller, followed by an integrated treatment with relatively constant voltage batteries attached to the electrode.

FIGS. 2 and 3 depict a battery powered, integrated treatment, with FIG. 2 showing current flow through the skin as a function of time without any pre-treatment or punch-through, whereas FIG. 3 displays current flow with the skin enhancement as a function of time after a punch-through treatment as shown in FIG. 5.

As known by those having ordinary skill in the art, iontophoresis dosage is typically specified as "milliAmp-minutes", which represents an accumulation of current flow over time. Therefore, the dosage in milliAmp-minutes can also be represented as the area underneath each of the two curves in FIGS. 2 and 3, integrating current over time. It should be obvious to one of ordinary skill in the art looking at the two graphs that in this case there is approximately twice as many milliAmp-minutes delivered post punch-through, than without any pre-treatment.

Referring back to FIG. 5, there is an optimal time for this punch-through pre-treatment, after which time there is little change in tissue resistance. In particular, the change in voltage and thus the change in tissue resistance is much smaller as a function of time on the right side of the graph with the current at 3 mA, than at the left before the current ramps down. It is further disclosed that this punch-through mode can be programmed such that it has a fixed time duration and current profile, or it could be optimized to any given patient and tissue. For example, the software/firmware in the dose controller can be programmed to look for a change in voltage as a function of time. It can be programmed to ramp down the current and complete the pre-treatment once the slope of the voltage or the absolute voltage itself is down below a selected threshold. This allows the pre-treatment time to vary from patient to patient, but would ensure an optimal lowering of the skin resistance.

Still another treatment option for the disclosed hybrid system is to proceed with a traditional treatment beyond any punch-through mode, be it optimized or not, but to not complete the entire treatment using traditional means. The traditional treatment can be interrupted after a period of time, for example 15 minutes, but prior to its completion of delivering the desired iontophoretic dose. There can be various means for informing the clinician of a remaining integrated treatment/wear time, based on a desired dosage and the amount of elapsed time using a traditional treatment. This can be provided in the form of a chart or table, or it can be programmed into the dose controller as a display option.

This calculation can be accomplished by knowing the desired target dose ($D_t$), the battery voltage built into the integrated patch ($V_b$), and the skin resistance ($R_c$) at $V_b$ as follows: $D_r=D_t-D_a$, wherein $D_r$=the remaining dose required after punch-through, and $D_a$=the accumulated dose through the punch-through and any subsequent traditional treatment phase.

The nominal current delivered by the integrated patch ($I_{int}$) can be calculated as follows: $I_{int}=V_b/R_c$. The remaining integrated treatment time ($t_{int}$) can then be estimated as follows: $t_{int}=D_r/I_{int}$. The integrated treatment time calculation can also be adjusted with a correction factor to address the skin resistance increasing slightly over the integrated treatment time.

In the above description, gender and/or patient weight may be specific in certain embodiments or descriptions. However, as will be appreciated by those having ordinary skill in the art, the present inventions should not be limited by gender and/or patient weight. Likewise, the invention should not be limited to preferred iontophoresis dosages of, for example, 40 milli-Amp-minutes or 80 milliAmp-minutes for either low voltage or traditional treatments. As will be appreciated by those having ordinary skill in the art, other dosages can be used without departing from the spirit of the invention.

In an embodiment, a connector system is provided that provides, among other things: 1) A receptacle that houses and positions on-board batteries in place, while ensuring proper orientation of battery polarity; 2) A coupling junction that maintains registered contact between the on-board batteries and current distribution element film conductive pathways; 3) Mechanical securing and electrically connecting an external electronic control module or power source or monitoring device to the patch, wherein this is accomplished with or without additional conductive or metallic crimp-mounted contacts or other contact landings or leads added to the current distribution element or to the connector device itself, and it utilizes only the printed conductive pathways on the current distribution element; and, 4) Automatically switching off and on the on-board battery electrical current upon connection to, an disconnection from, an external control or power source.

As indicated above, the connector combines several individual functional elements into an injection-molded plastic body assembly that satisfies multiple design constraints, while eliminating typically required extraneous components (e.g., switch contacts, metallic battery tabs, soldered or crimped connectors, conductive coupling joints, etc.). The injection-molded body works in conjunction with the current distribution element, a required component in most modern iontophoresis electrode devices.

As explained in detail further herein, the connector and the current distribution element work in conjunction with an external controller or power supply or monitoring device via electrical contact pins mounted within the external device itself. The pins are used to communicate electrically with the connector. Furthermore, the external device mounts to the connector during such operation.

As will be appreciated by those having ordinary skill in the art, typically an iontophoresis current distribution element is comprised of a non-conductive substrate film (e.g. commonly, polyester film) upon which silk-screen printed patterns of various conductive and dielectric (i.e., insulative) inks are deposited. The graphic design of the pattern or symbol that is printed on the polyester film is generally inconsequential to cost or manufacturing time. After these image patterns are printed and cured onto the film, the current distribution element components are die-cut in order to yield a completed part of a particular size and shape for application into the electrode patch. Similarly as in printing, the complexity of the die-cut shape does not generally affect cost or manufacturing time. As such, any additional ink pathway traces, dielectric masking, and holes punched required in the final die-cut procedure do not add processing complexity or cost to the current distribution element for the connector device or system.

In an embodiment in accordance with the present invention, the current distribution element design that functions with the connector device generally contains the same amount of ink and film components, the same general degree of process steps, and consequently would generally cost no more than would a current distribution element in a standard type commercially available integrated iontophoresis electrode patch. This is a benefit of the design worthy of mention, as some multifunctional systems conversely demand greater process complexity and hence increased cost.

Moreover, in an embodiment in accordance with the present invention, an advantage of the connector device design is that it performs the same functions by using a single plastic part assembly, as would an equivalent system that employs several components to achieve equivalent results. In manufacturing, this offers a clear advantage in fabrication processing, as a timesaving can be realized due to less assembly time, and also a labor cost savings. Furthermore, the cost of a single plastic part assembly is typically less that the accumulated costs of several components. Additionally there are fewer components to encounter manufacturing errors, or to experience part failures or defects, hence reliability is improved.

Figure 20:
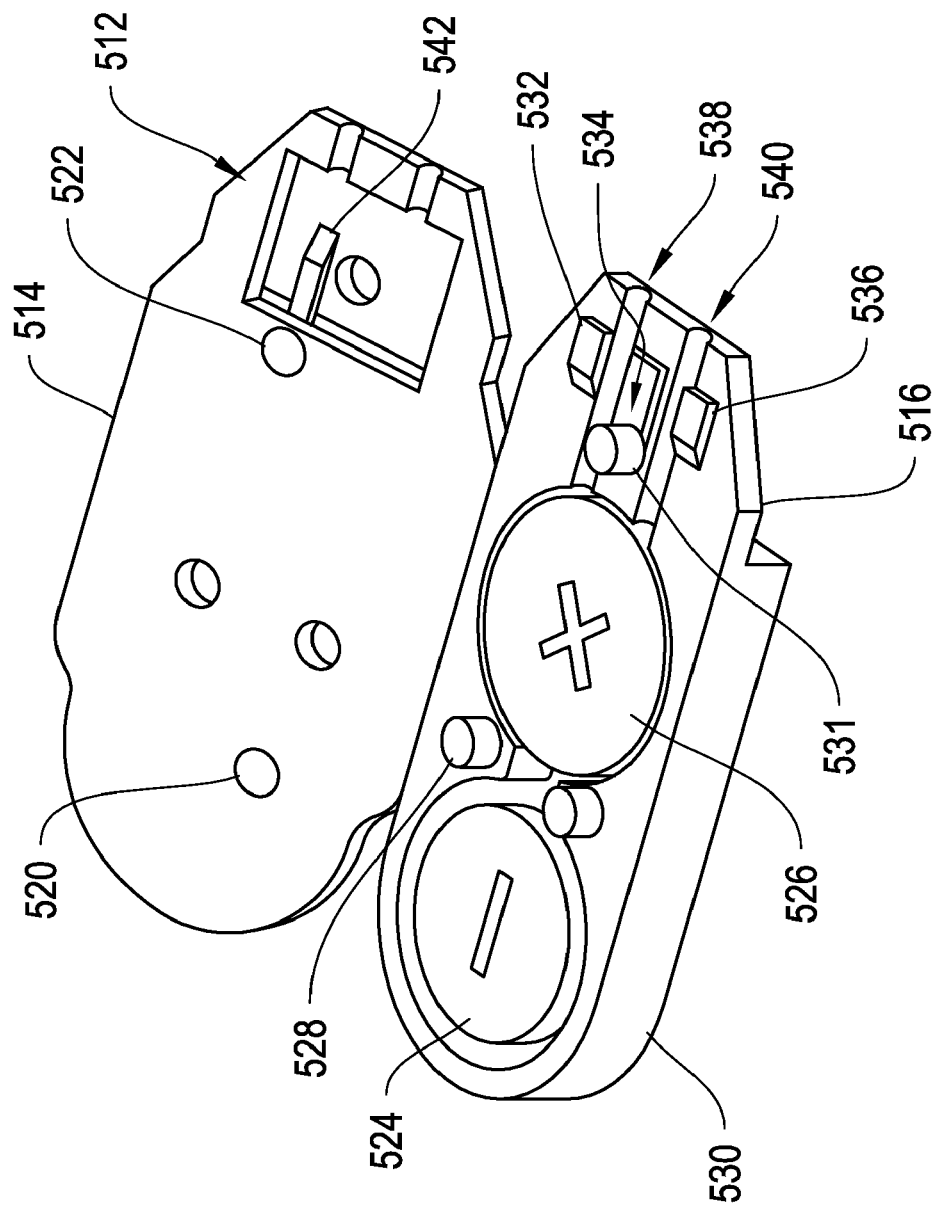
FIG. 20 is a prospective view of a connector in accordance with the present invention and having a lid and base with batteries contained therein.

Turning to FIG. 20, an embodiment of a connector casing or body in accordance with the present invention is illustrated. The connector body 512 is preferably a plastic part having a lid 514 and a base 516. Pressure nodes 520,522 are molded features within the lid 514. As the lid 514 hinges closed (a flexible plastic "living" hinge in this example) to fully encapsulate the batteries 524,526, these nodes 520,522 will create high pressure at pre-defined contact points on the current distribution element (not shown), providing electrical contact between the batteries 524,526 and current distribution element. In an embodiment, an extension strip or conductive path can be included that serves as a jumper lead for connecting the button cell batteries.

In FIG. 20, the registering pegs 528-31 serve to guide and position the current distribution element 612 (FIG. 21) properly relative to the connector case lid 514 and base 516.

Figure 21:
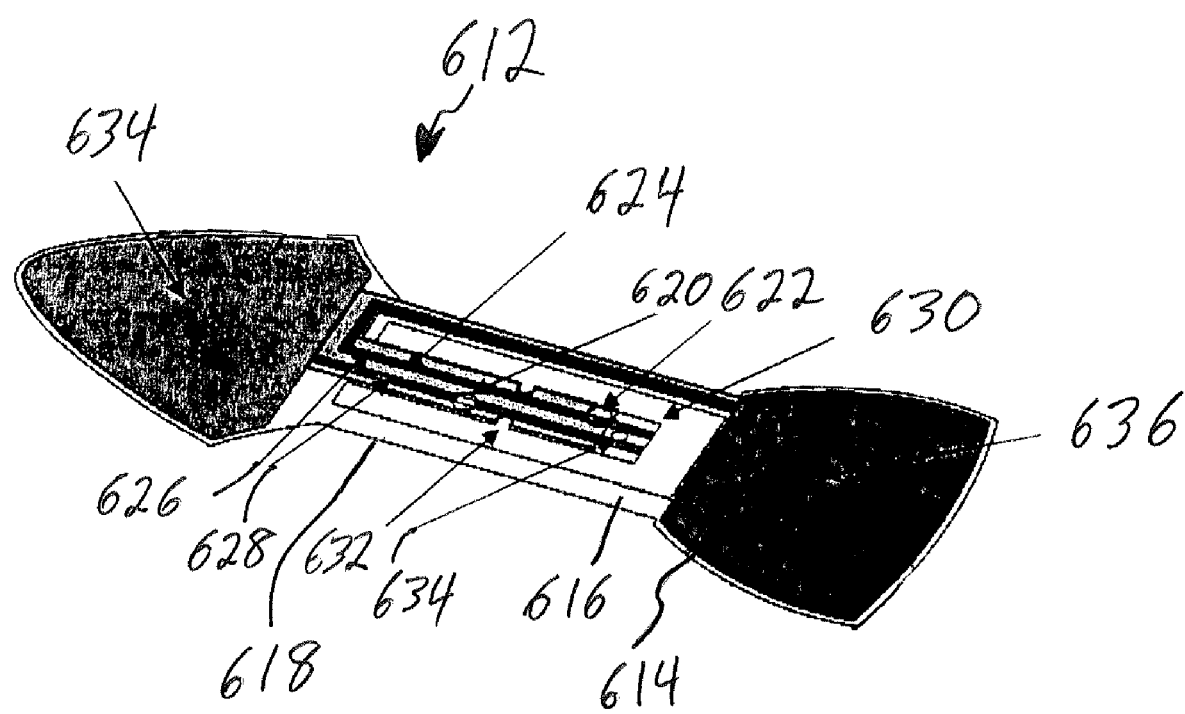
FIG. 21 is a perspective view of a current distribution element in accordance with the present invention and for use with the connector of FIG. 20.
Figure 22A:
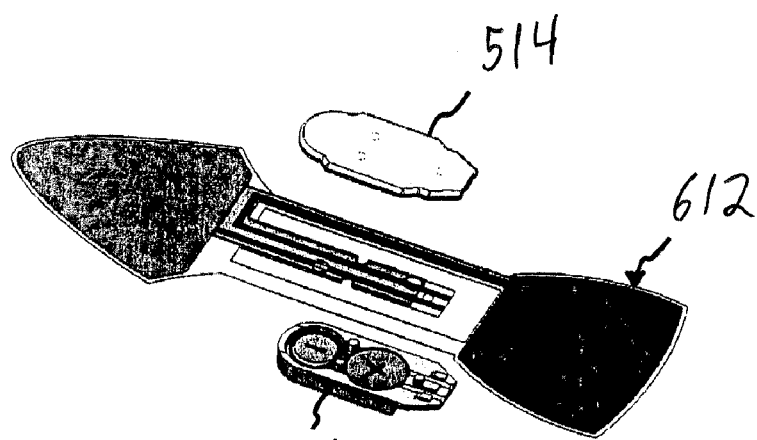
FIG. 22(A) is an exploded view of the connector of FIG. 20 with the current distribution element of FIG. 21 positioned therebetween.
Figure 22B:
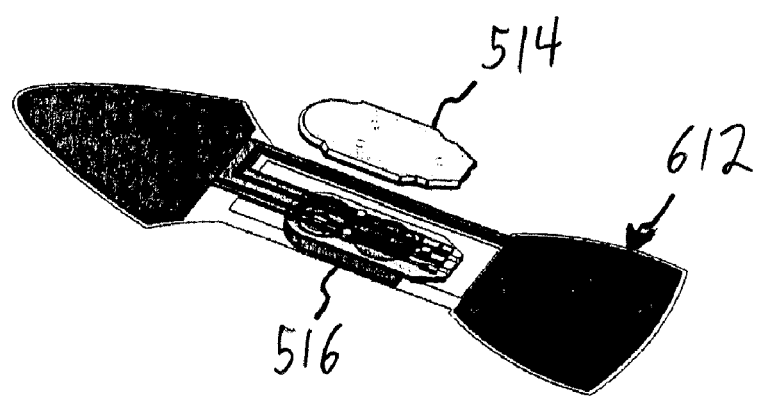
FIG. 22(B) is similar to FIG. 22(A), but with the current distribution element of FIG. 21 located in place in the base of the connector of FIG. 20.
Figure 22C:
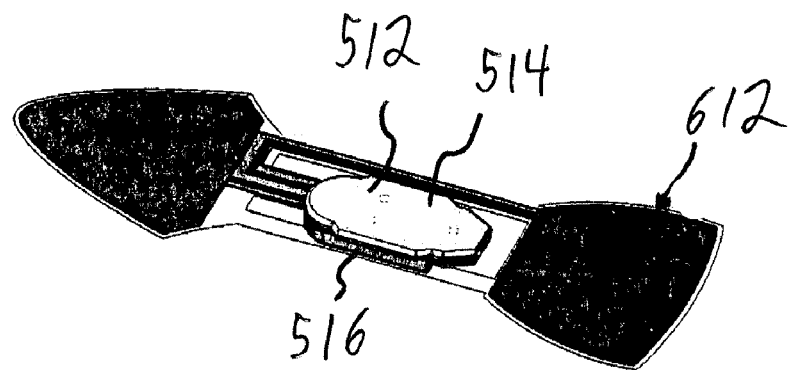
FIG. 22(C) is similar to FIG. 22(B), but with the current distribution element of FIG. 21 fully assembled into the connector of FIG. 20 to form an electrode patch assembly with a connector attached.

Further, within the base 516, the film stays 532-36 function to raise and press the surface of the current distribution element film 612 (FIG. 21) up to the top edge of the pin insert ports 538,540. The pins on the external module device (not shown) can then readily contact the current distribution element conductive pathways (not shown) upon insertion. Moreover, the switch-pin ramp 542 deflects the connector lid 514 slightly when the external pins 711,712 (FIG. 24B) are inserted. This deflection causes the pressure node 522 above battery 526 to lift, disconnecting the battery from the current distribution element 612 (FIG. 21). The resultant spread or expansion of the connector serves to wedge or secure the external controller to the connector.

Turning to FIG. 21, an embodiment of a current distribution element in accordance with the present invention is illustrated. The current distribution element 612 includes a polyester film substrate 614 comprising a transparent material, and the up-facing surface 616 of the current distribution element the depiction of FIG. 21 has no ink printed on it. So, the entire up-facing surface 616 is non-conductive because it is the plastic-only side. The observer from this view is able to view the inks only because the substrate is clear (like viewing painted images on the back side of a glass pane). Conversely, the down-facing surface 618 is the side that is printed with the inks.

The current distribution element 612 includes battery contact windows 620,622 comprising unmasked regions in a dielectric insulative ink layer 624, which allows conductive pathways 626,628 to be exposed at those points.

Turning back to FIG. 20, the pressure nodes 520,522 in the connector lid 514 contact the battery contact windows 620, 622 (FIG. 21) in the current distribution element 612 and force the conductive pathways 626,628 into electrical communication with the batteries 524,526. Not shown in FIG. 20 is a jumper strip that connects the two down-facing terminals of the batteries together to allow an in-series connection. This jumper strip may be comprised of resistive material such as carbon film, in order to impose a safety limit on the amount of electrical current delivered in case of comprised skin. This jumper strip can be built-in or printed on, as an extension to the current distribution element for enhanced manufacturability or simplification.

Going back to FIG. 21, the portion of the current distribution element 612 that mounts into the connector 512 (FIG. 20) is the center tongue 630, and there are two strips of the current distribution element film that lie on either side. One of the side strips is printed with a conductive trace and insulated with dielectric ink, leading to the cathode 636. The other side strip features no ink, and is simply retained for support. Along the dielectric masked portions of the tongue, the batteries are safely insulated from contact.

Contact with external device pins (e.g. electronic controller of FIG. 24) is made near the edge of the tongue, where the conductive pathways terminate at the distal end. The exposed conductive pathways are not masked with dielectric insulative ink in this region. Further, registration holes 632,634 serve to position the current distribution element 612 properly relative to the connector registration pegs 528-31 (FIG. 20).

Figure 25:
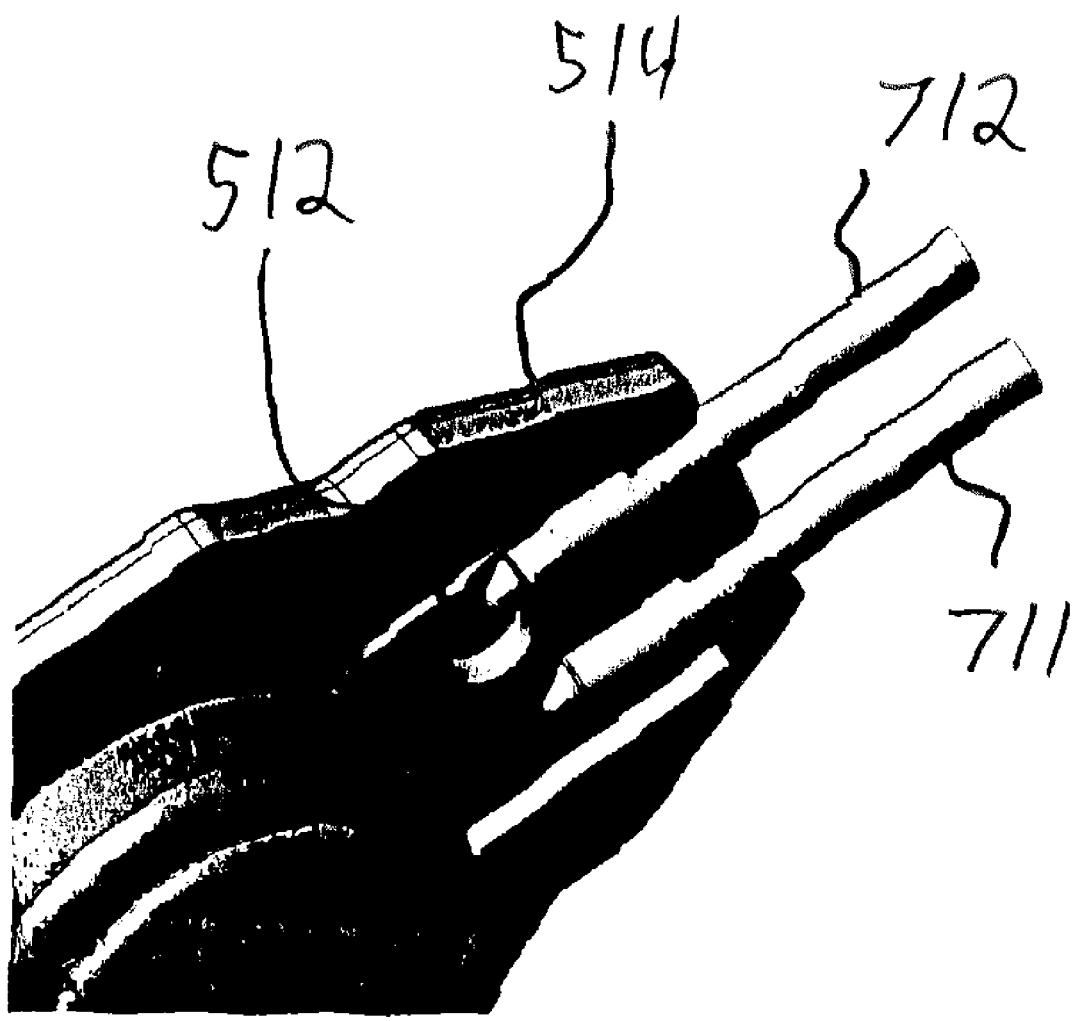
FIG. 25 is a detailed view of the pins of FIG. 24(B) being received within the connector of FIG. 20 and approaching a switch-pin ramp.
Figure 26:
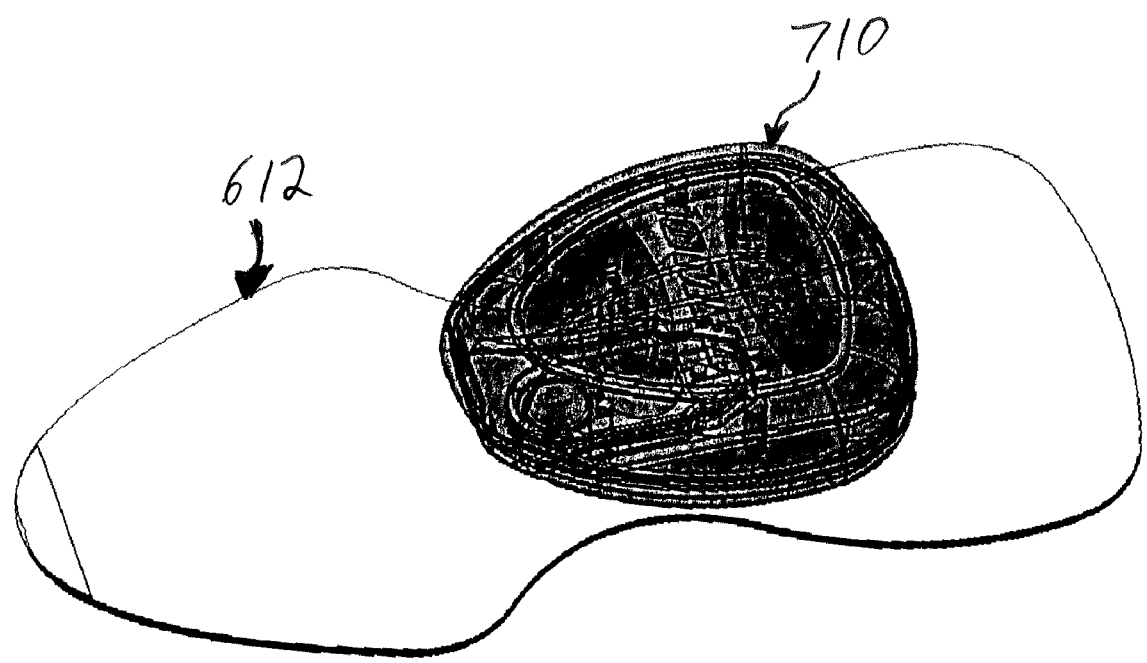
FIG. 26 depicts the controller of FIG. 24(A) attached to the patch of FIG. 23(A) wherein the controller and connector are ghosted.

Turning to FIG. 25, an illustration is provided of inserting pins 711,712 further, progressively contacting the ramp 542 and causing the connector lid 515 to deflect upwards. This is the action that is responsible for disconnecting the battery 526 from the current distribution element 612 (FIG. 21) as the pins 711,712 engage into the connector 512.

Figure 23A:
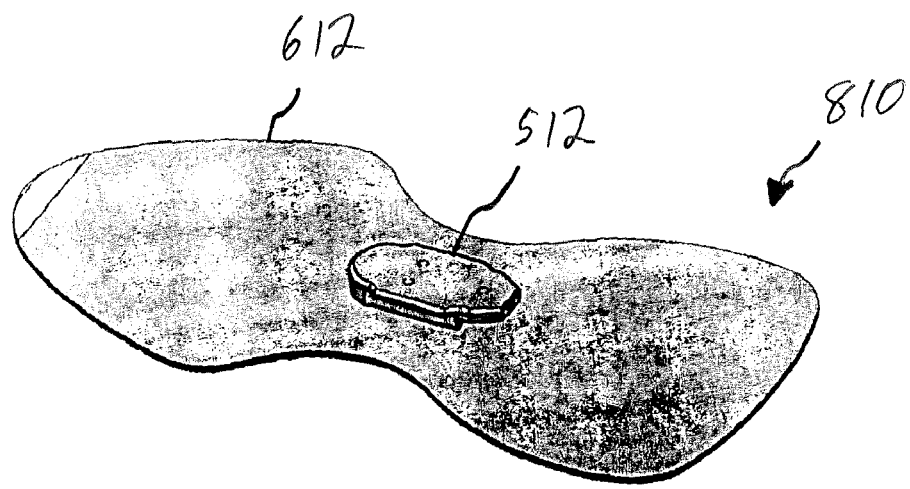
FIG. 23(A) is a top surface view of an electrode patch assembly with the connector attached.
Figure 23B:
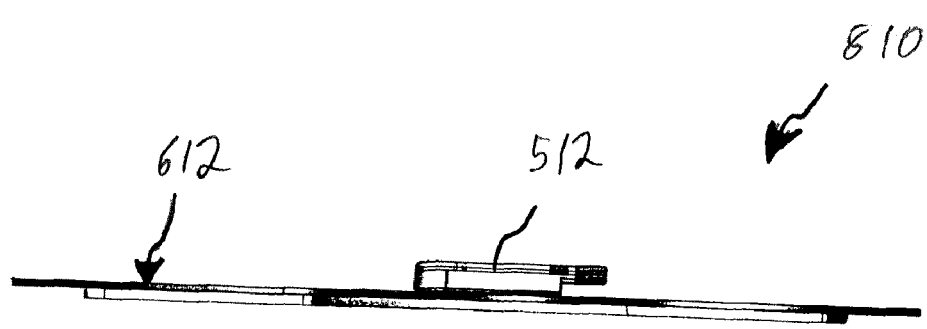
FIG. 23(B) is a side view of the electrode patch assembly of FIG. 23(A)
Figure 23C:
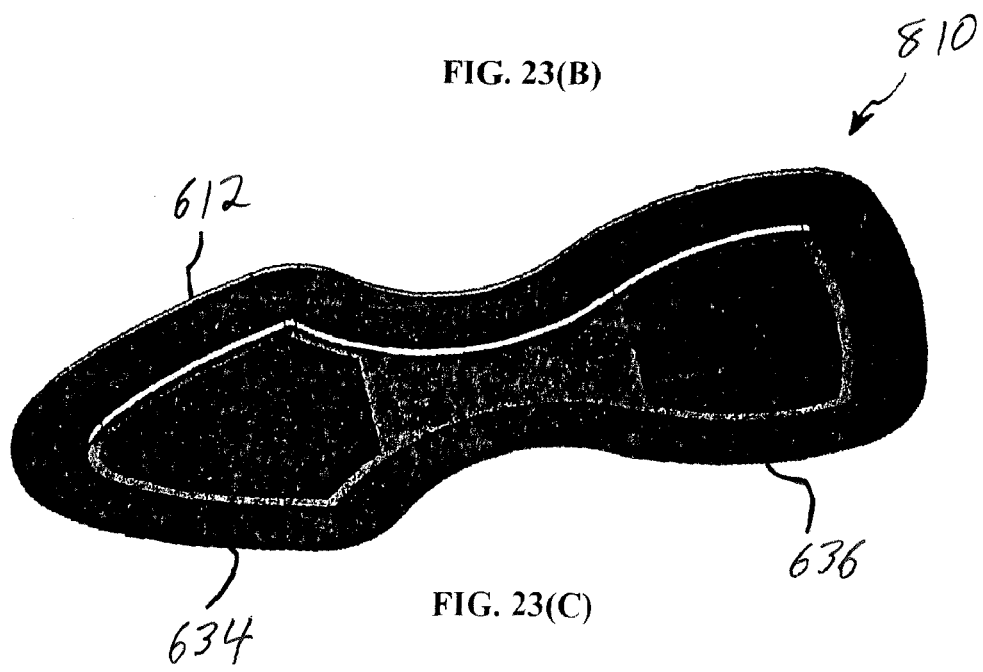
FIG. 23(C) is an underside view of the electrode patch assembly of FIG. 23(A)

Turning to FIG. 23C, at the anode 634 of the surface of the patch 810 that attaches to a patient, the surface portion can be hydrated with a saline or contain a conductive material such as a gel that does not need to be hydrated. Also, at the cathode 636 of the surface of the patch 810 that attaches to a patient, the surface portion can have a medicament thereon. In yet another embodiment, the anode can have a medicament thereon and the cathode can be hydrated with a saline or contain a conductive material such as a gel that does not need to be hydrated. Additional contacts can be designed into the current distribution element along with additional pins or pin locations in the external controller for the purpose of detecting or selecting different treatment modes when the controller is attached to the electrode.

Figure 24A:
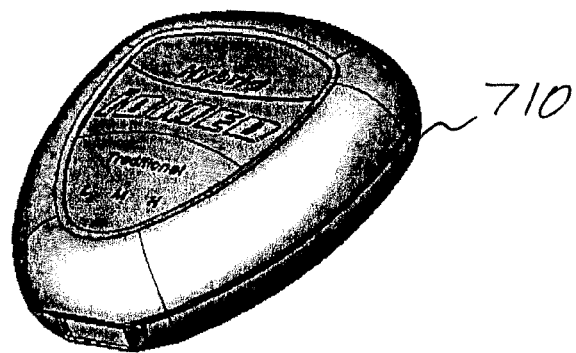
FIG. 24(A) is a perspective view of a controller module.
Figure 24B:
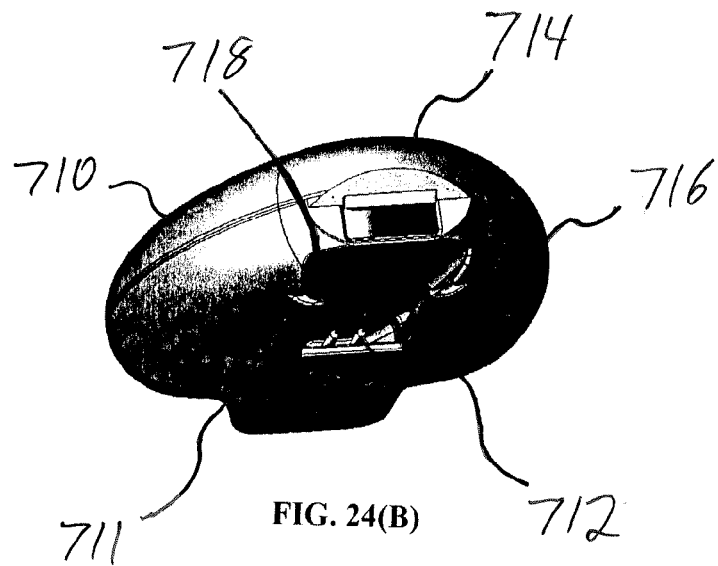
FIG. 24(B) is another view of the controller module of FIG. 24(A) wherein pins for insertion into the connector of FIG. 20 are shown.
Figure 24C:
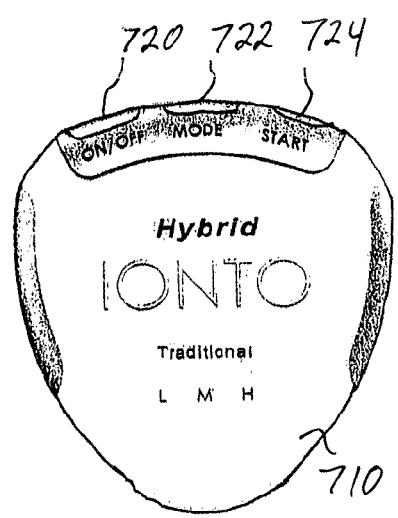
FIG. 24(C) is a top view of the controller module of FIG. 24(A)

Turning to FIGS. 24A-24C, in an embodiment, the outer surface 714 to the plastic housing 716 of the removable controller 710 can have indicia or color coding thereon to specify the iontophoretic treatment type provided by the removable controller 710. For instance, the housing 716 can be colored blue to indicate a low voltage treatment, yellow to indicate a medium voltage treatment, and green to indicate a high voltage treatment.

The controller 710 can also include a plurality of buttons 720-24 for turning the controller off and on, starting the treatment method, and selecting the treatment method to be provided by the controller. For instance, the treatment method can be selected from traditional, integrated patch, or hybrid. In an embodiment, the traditional iontophoresis method can include the steps of applying the controller 710 to the patch 810 for 10-20 minutes to provide a 40 mA-minute treatment. In an embodiment, the integrated patch method can include the steps of applying the patch 810 to the treatment area for 6 hours to provide an 80 mA-minute treatment. In an embodiment, the hybrid method can include the steps of applying the controller 710 to the patch 810 for 3 minutes to lower resistance or enhance conductivity in the skin to enhance drug delivery, then the controller is removed and the patient wears the patch for 3 hours to provide an 80 mA-minute treatment. Preferably, the mode button 722 can be used to select the traditional iontophoresis mode to be applied by the controller at one of three predefined current setting.

In another embodiment, a docking station (not shown) can be provided for the controller 710, wherein the docking station provides data to the controller. For instance, the controller 710 can be removably mounted to the docking station wherein the docking station programs the controller, via a user input such a switch, to provide a treatment type (i.e., high, medium or low voltage) for a user defined period of time once the controller is attached to a patch (i.e., current distribution element 612). Accordingly, a more miniaturized or less expensive controller can result.

In yet another embodiment, a recharging station (not shown) can be provided to charge rechargeable batteries within the controller 710. In an embodiment, a fully charged controller can be used up to ten times before it needs to be recharged. The recharging station can include a series of lights that will inform a user of the charging status of the controller. In an embodiment, the lights can be LEDs to provide a color indicating that the controller is being charged, another color indicating that the controller is charged, another color to indicate that charging has failed to occur, and yet another color to indicate a thermal error.

Alternative, the controller 710 and the connector 512 on the patch 612 can have means whereby the controller can identify the connector and, in response thereto, provide a specific treatment type. For instance, the connector can have jumpers therein and the controller can detect the position of the jumpers, via electrical means, and provide a treatment in response to the setting of the jumpers. The jumpers can be conventional metal bridges, fused links, or software controlled.

In an embodiment, to ensure that the correct controller 710 is attached to the connector 512 of the patch 612, the connector and the passage 718 in the controller for receiving the connector can be keyed. For instance, controllers for providing a low, medium or high voltage treatment are keyed to attach only to connectors of patches for providing the low, medium or high voltage treatment, respectively.

In an embodiment, the connector can include one or more additional electrical contact nodes between the printed resistors or printed paths. The serves to identify a specific path or families of patches, providing information to the processor in order to specify dosing profiles and current output.

In a further embodiment, the connector can be a) used with two or fewer batteries, b) used with fewer batteries than the maximum possible, c) used with a single battery, d) used with no batteries, e) used to either connect a sole external battery pack and/or to supplement the on-board batteries with additional external batteries so that its role is a power plus supply and connector, and/or to connect to external power source(s) for the purpose of recharging the batteries-on-board the connector. It can be utilized in any or all of these alternatives within a single design, not necessarily separate embodiments. For example, the design described above is capable of using two batteries, one battery, or no batteries without changing the design at all. For housing rechargeable batteries, one simply modifies the existing printed pathways on the CDE and relocate the contact pressure nods on the connector lid.

In another embodiment, the connector can be either permanently closed and sealed (for single use) and/or it is able to be opened for battery replacement if desired and necessary. Further, the connector can include nested walls for hosting various sizes of coin cell batteries, which would serve to make the connector more versatile.

In yet another embodiment, an individual or set of manually insertable plug(s), cap(s), pin(s), key(s), removable plug(s), cap(s), pin(s), key(s), either color coded, electronically coded, numbered, or other methods of distinction, that serve to initiate and deliver functions the connector inherently features by triggering additional switching, such as: a) battery connection to switch the patch to active; b) battery disconnection to switch the patch to an inactive state, c) trigger and initiate one or more specific conductive or resistive path(s) or on-board circuits of several in order to select a particular circuit resistance, define a desired polarity, or adjust duration by means of guiding electrical activity to specific chemo-sacrificial or electrically controlled CDE pads.

In a further embodiment, a connector design is provided that can either switch multiple times or be limited to just one single cycle via a breakable feature included in the plastic lid and the CDE. A single switching cycle allows the product to turn off only once, and for all, or alternatively turn on only once, and for all, insuring batteries or chemo-limiting feature(s) have been depleted, and/or discouraging or elimination tampering.

Turning to the controller, in an embodiment, the controller is applied to the patient in a motion requiring only forces that are independent of the direction of pressure that might otherwise inflict pain to a sore or injured body site. Moreover, although the IDC is primarily a device that eliminates the need for connecting via wire, it can also be used in conjunction with wires. If a particular application or condition should require or is better served by placing the IDC remotely from the patch, then it can provide for that alternative as well. In addition, an adaptor can be provided with wires tethered.

In an embodiment, multiple pins can be provided to communicate with the connector(s) or other connector(s), to improve diagnostics via a third independent grounding lead, additional switching, and the like.

As previously stated above, an indicator can be provided indicate completion of the second-stage, low voltage treatment, or the only-stage-low-voltage treatment (i.e., non punch through, on board batteries only). Among other indicating methods, this can include a color change of the CDE, as is characteristically demonstrated with Ag–>AgCl oxidization of the anode. The patch can include a like-colored swatch of grey ink printed on the CDE so the patient or clinician can compare the grey print to the Ag anode and determine when the CDE gets dark enough (i.e., sufficiently "un-silver") to it to be determined that treatment is complete. Since the CDE substrate is transparent PET film, the color comparative swath can be printed either on the non-active side of the CDE substrate, or as first-layer on the active side beneath the Ag ink layer.

It should be emphasized that the above-described embodiments of the present invention, particularly, any "preferred" embodiments, are possible examples of implementations merely set forth for a clear understanding of the principles of the invention. Many variations and modifications may be made to the above-described embodiment(s) of the invention without substantially departing from the spirit and principles of the invention. All such modifications are intended to be included herein within the scope of the disclosure and the present invention, and protected by the following claims.

What is claimed is:

1. An apparatus for applying an iontophoretic transdermal process to a body site comprising:
    a treatment delivery unit, including first and second power supplies, configured to:
    receive a selection of one of a plurality of treatment modes; and deliver:
    using the first power supply but not the second power supply, the selected one of the plurality of treatment modes to the body site;
    using the second power supply, after using the first power supply, a low voltage iontophoretic transdermal patch treatment to the body site.

2. The apparatus of claim 1 wherein delivering a selected one of the plurality of treatment modes to the body site comprises delivering about 2 milliAmps when a low current mode is selected, delivering about 3 milliAmps when a medium current mode is selected, and delivering about 4 milliAmps when a high current mode is selected.

3. The apparatus of claim 1 wherein delivering a selected one of the plurality of treatment modes to the body site comprises delivering about 0.5 milliAmps when a low current mode is selected, delivering about 1 milliAmp when a medium current mode is selected, and delivering about 1.5 milliAmps when a high current mode is selected.

4. The apparatus of claim 1 further comprising at least one of a thumbwheel, dial or membrane switch operable to adjust the treatment delivered when one of the plurality of treatment modes is selected.

5. The apparatus of claim 1 wherein the treatment delivery unit comprises a controller mounted to an iontophoretic patch.

6. The apparatus of claim 1 wherein the treatment delivery unit comprises a controller operatively attached to a connector integral to an iontophoretic patch.

7. The apparatus of claim 1 wherein the plurality of treatment modes includes a body site conductivity enhancement mode.

8. The apparatus of claim 7 wherein delivering the body site conductivity enhancement mode comprises applying a current of about 3 milliAmps to the body site.

9. The apparatus of claim 7 wherein delivering the body site conductivity enhancement mode comprises applying a current in the range of about 0.1 to 4 milliAmps to the body site.

10. The apparatus of claim 7 wherein delivering the body site conductivity enhancement mode comprises applying a current density of 0.53 milliAmp/centimeters$^2$, or less, to the body site.

11. The apparatus of claim 1 wherein the second power supply is integral to the iontophoretic patch.

12. The apparatus of claim 7 further comprising an indicator to provide a warning if the electrical conductivity of the body site has not been adequately enhanced at the completion of the delivery of the body site conductivity enhancement mode.

13. The apparatus of claim 1 wherein the second power supply is a disposable power source.

14. An apparatus comprising an iontophoresis controller having a housing keyed to a connector mounted to an iontophoretic patch, wherein:
the housing is removably engageable with the iontophoretic patch via the connector, and
the iontophoretic patch is capable of delivering a first iontophoresis treatment when the controller is engaged and a second iontophoresis treatment when the controller is disengaged.

15. The apparatus of claim 14 wherein the keying is based on a medicine to be applied.

16. The apparatus of claim 14 wherein the iontophoresis controller includes a first power supply.

17. The apparatus of claim 16 wherein the first iontophoresis treatment is provided using the first power supply.

18. The apparatus of claim 14 wherein a second power supply included in the iontophoretic patch is bypassed during the first iontophoresis treatment.

19. The apparatus of claim 16 wherein the first power supply is a rechargeable battery.

20. The apparatus of claim 14 wherein the second iontophoretic treatment is mechanically triggered by disengaging the controller from the iontophoretic patch.

21. The apparatus of claim 18, wherein contact between the iontophoretic patch and the second power supply is deflected when the controller is engaged.

22. The apparatus of claim 14 wherein the second iontophoretic treatment is electrically triggered by disengaging the controller from the iontophoretic patch.

23. The apparatus of claim 22, further comprising a transistor switch for electrically triggering the second iontophoretic treatment by disengaging the controller from the iontophoretic patch.

24. The apparatus of claim 14 wherein the second iontophoretic treatment is triggered by the completion of the first iontophoresis treatment.

25. The apparatus of claim 14 wherein the iontophoretic patch includes a disposable power supply.

26. The apparatus of claim 14, wherein the housing is keyed to the connector via a plurality of electrical contact pins.

27. The apparatus of claim 26 wherein the first iontophoresis treatment is based on the keying.

28. The apparatus of claim 26 wherein the keying is based on a voltage level to be used in the first iontophoretic treatment.

29. The apparatus of claim 26, wherein the keying is based on the position of one or more jumpers included in the connector.

30. The apparatus of claim 14, wherein the connector includes one or more electrical contact nodes which identify the iontophoretic patch to the controller.

31. The apparatus of claim 7, wherein delivering the body site conductivity enhancement mode comprises applying a current to the body site over a time period of between about 1.2 minutes and about 3 minutes.

32. The apparatus of claim 1 wherein the first and second power supplies are selectively operable.

33. The apparatus of claim 6, wherein the controller is operatively attached to the iontophoretic patch via a plurality of electrical contact pins.

* * * * *